United States Patent [19]
Calvet et al.

[11] Patent Number: 6,013,656
[45] Date of Patent: *Jan. 11, 2000

[54] 2-(ARYLALKENYL) AZACYCLOALKANE DERIVATIVES AS LIGANDS FOR SIGMA RECEPTORS

[75] Inventors: Alain Pierre Calvet, L'Hay-les-Roses; Henry Jacobelli, Paray-Vieille-Poste; Jean-Louis Junien, Sévres; Pierre Riviere, Paris; François-Joseph Roman, Vitry-sur-Seine, all of France

[73] Assignee: Warner-Lambert Company, Morris Plains, N.J.

[ * ] Notice: This patent is subject to a terminal disclaimer.

[21] Appl. No.: 09/145,918

[22] Filed: Sep. 2, 1998

Related U.S. Application Data

[62] Division of application No. 08/652,567, Jun. 7, 1996, Pat. No. 5,849,760, which is a continuation of application No. PCT/FR94/01439, Dec. 9, 1994.

[30] Foreign Application Priority Data

Dec. 9, 1993 [FR] France ..................... 93 14814

[51] Int. Cl.⁷ ....................... A61K 31/445; C07D 211/14
[52] U.S. Cl. ..................... 514/317; 514/212; 514/318; 514/319; 514/320; 514/408; 540/484; 546/192; 546/195; 546/205; 546/213; 548/400; 548/579
[58] Field of Search ..................... 514/212, 317, 514/318, 319, 350, 408; 540/484; 546/192, 195, 205, 213; 548/400, 579

[56] References Cited

U.S. PATENT DOCUMENTS

| | | | |
|---|---|---|---|
| 5,034,419 | 7/1991 | Aubard et al. | 514/649 |
| 5,089,639 | 2/1992 | Aubard et al. | 549/491 |

FOREIGN PATENT DOCUMENTS

| | | |
|---|---|---|
| 40899/89 | 6/1992 | Australia . |
| 71340/91 | 5/1993 | Australia . |
| 0361990 | 4/1990 | European Pat. Off. . |
| 0362001A1 | 4/1990 | European Pat. Off. . |
| 0445013A1 | 9/1991 | European Pat. Off. . |
| 92/18127 | 10/1990 | WIPO . |
| 91/03243 | 5/1991 | WIPO . |
| 91/06297 | 5/1991 | WIPO . |
| 91/09594 | 7/1991 | WIPO . |
| 92/22527 | 12/1992 | WIPO . |
| 93/09094 | 5/1993 | WIPO . |
| 93/15052 | 8/1993 | WIPO . |

OTHER PUBLICATIONS

Goldner, F. H., and Kraft, S. C., "Idopathic Inflammatory Bowel Disease," *Internal Medicine*, 4$^{th}$ ed., J. H. Stein, editor, (St. Louis: Mosby, 1994), pp. 458–470.

Stein, J. H., et al., *Internal Medicine*, 4$^{th}$ ed., J. H. Stein, (St. Louis, Mosby, 1994), pp. 443–445.

PCT International Search Report, mailing date Dec. 9, 1994.

*Primary Examiner*—Richard L. Raymond
*Attorney, Agent, or Firm*—Charles W. Ashbrook

[57] ABSTRACT

New 2-(arylalkenyl)azacycloalkane derivatives which are ligands for sigma receptors, of the formula (I)

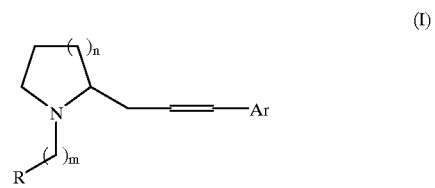

in which:
  Ar is aryl or heteroaryl, optionally mono- to trisubstituted,
  m has the value 1 or 2,
  n has the value 1 to 3,
  R is phenyl, or cycloalkyl containing 3 to 7 carbon atoms,
  their isomers and their addition salts.

Medicinal drugs which are antipsychotic agents and are useful in gastroenterology.

5 Claims, 2 Drawing Sheets

2-(ARYLALKENYL) AZACYCLOALKANE DERIVATIVES AS LIGANDS FOR SIGMA RECEPTORS

CROSS-REFERENCE TO RELATED APPLICATION

This application is a divisional of U.S. patent application Ser. No. 08/652,567 filed Jun. 7, 1996, now U.S. Pat. No. 5,849,760, which is a continuation of PCT/FR94/01439 filed Dec. 9, 1994.

FIELD OF THE INVENTION

This invention relates to new compounds derived from 2-(arylalkenyl)azacycloalkanes which are in vitro ligands for sigma ($\sigma$) receptors and are potentially useful in the treatment of gastrointestinal complaints and in the treatment of neurological disorders and/or psychotic states.

TECHNOLOGICAL BACKGROUND OF THE INVENTION

European Patent Application 362,001 describes $\alpha,\alpha$-disubstituted N-cycloalkylalkylamines having specific affinity for sigma ($\sigma$) receptors and which are useful in the treatment of psychoses and gastrointestinal complaints, of the formula

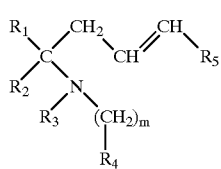

(I)

in which:
$R_1$ and $R_5$ are phenyl, $R_2$ is alkyl, $R_3$ is hydrogen or low-molecular-weight alkyl, $R_4$ is cycloalkyl, m is 1 or 2.

European Patent Application 445,013 describes N-cycloalkylalkylamines having specific affinity for $\sigma$ receptors and which are useful in the treatment of psychoses and gastrointestinal complaints, of the formula

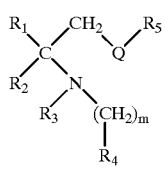

(I)

in which:
$R_1$ is a furyl or thienyl radical or alternatively a phenyl radical, provided that Q is 1,2-cyclopropanediyl, $R_2$ is low-molecular-weight alkyl, $R_3$ is hydrogen or low-molecular-weight alkyl, m has the value 1 or 2, $R_4$ is cycloalkyl—$CH(CH_2)_n$, in which n is from 2 to 5, $R_5$ is phenyl or thienyl, Q is 1,2-ethylenediyl or 1,2-cyclopropanediyl.

Although displaying an affinity for the same types of receptors as the compounds of this invention, the amines disclosed in these two documents differ in terms of their structure, which is that of amines in which the nitrogen atom is not included in a cycloalkane sequence.

PCT Application WO 91/03243 includes a description of 1-cycloalkylpiperidines having specific antagonist activity toward $\sigma$ receptors and which are useful in the treatment of psychoses and dyskinesias, of the formula

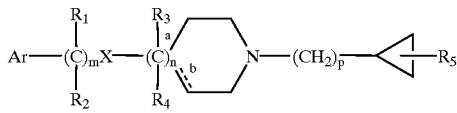

(I)

in which, preferably:
X is C=O, CHOH or O; and/or m is 0; and/or n and p are 1; and/or $R_3$–$R_5$ are H; and/or Ar is phenyl, optionally substituted by halogens, $OCH_3$, $NH_2$, $NO_2$ or another phenyl group, a and b representing, moreover, single bonds or either of them representing a double bond.

PCT Application WO 93/09094 includes a description of ethers derived from alkyl piperidines or pyrrolidines which are antipsychotic agents, of the formula

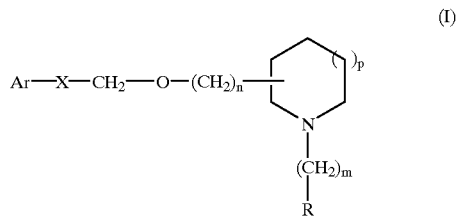

(I)

in which, for the preferred compounds:
n and p are 1; and/or m is 1–3; and/or R is phenyl; and/or X is trans —CH=CH—; and/or Ar is phenyl, p-F-phenyl or p-$CF_3$-phenyl; and/or the side chain is located at position 4 of the piperidine ring.

Among other dissimilarities, the compounds of PCT applications WO 91/03243 and WO 93/09094 differ formally from the compounds of the present invention by the existence in their intermediate chain of an oxygen-containing function (C=O, CHOH) or an oxygen atom —O—. It is also noteworthy that this chain is located, or is declared to be preferably linked to the carbon atom, at position 4 (para) of the piperidine ring, and in no case on the carbon atom at position 2, adjacent to the nitrogen atom. These applications do not make mention of any use of the compounds for the treatment of gastrointestinal complaints.

PCT Application WO 92/22527 describes calcium-channel-antagonist compounds of the formula

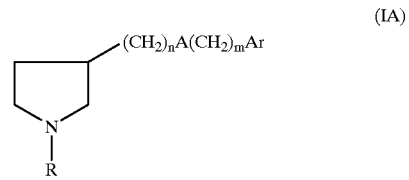

(IA)

in which, inter alia:
R is ($C_{1-8}$ alkyl) ($C_{3-8}$ cycloalkyl); p [sic] is 0 to 2; n is 0 to 6; A is —CH=CH—; Ar is aryl.

PCT Application WO 93/15052 describes calcium-channel-antagonist compounds of the formula (I<sub>B</sub>)

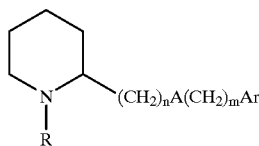

in which, Ar being optionally substituted aryl or heteroaryl, it is defined for the preferred compounds that: m has the value 0 to 3, R is ($C_{1-8}$ alkyl) (phenyl)p in which p is 0 or 1, or R is ($C_{2-8}$ alkenyl) (phenyl)p in which p is 1, A is oxygen or —CH=CH—, the length of the —$(CH_2)_n$A$(CH_2)_m$— chain being from 2 to 6 atoms.

These latter two applications relate to compounds which are calcium channel antagonists and which differ from the compounds of the present invention by virtue of that use. Moreover, contrary to what might be assumed from the declared meanings of R, A, Ar, n and m, none of the compounds referred to in these documents is prejudicial to the novelty of the 2-(alkenyl)azacycloalkanes (I) to which the present invention relates.

SUMMARY OF THE INVENTION

The invention relates to new 2-(arylalkenyl) azacycloalkane derivatives of the formula (I)

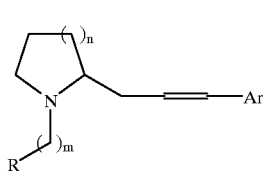

in which Ar is aryl or heteroaryl, optionally mono- di trisubstituted, m has the value of 1 or 2, R is phenyl, optionally substituted, or cycloalkyl containing 3 to 7 carbon atoms, n has the value of 1 to 3, their isomers, their derivatives in which an atom is replaced by one of its radioactive isotopes, and their addition salts with the pharmaceutically acceptable acids.

The compounds of the invention show an especially advantageous affinity in vitro for σ receptors, which is indicative of their usefulness in the prevention or treatment of neurological disorders and/or psychotic states; and, in vivo, they show a pharmacological activity which is especially indicative of their usefulness in the treatment of gastrointestinal complaints.

The preferred compounds of the invention are those in which:

Ar is an optionally substituted phenyl radical, n is 1 or 2,

R is a cyclopropyl, cyclobutyl or phenyl radical.

The present invention also relates to the process for the preparation of the azacycloalkanes (I) and to pharmaceutical compositions comprising a compound (I) in combination with pharmaceutically acceptable excipients, diluents or solvents.

DETAILED DESCRIPTION OF THE INVENTION

Figure 1:
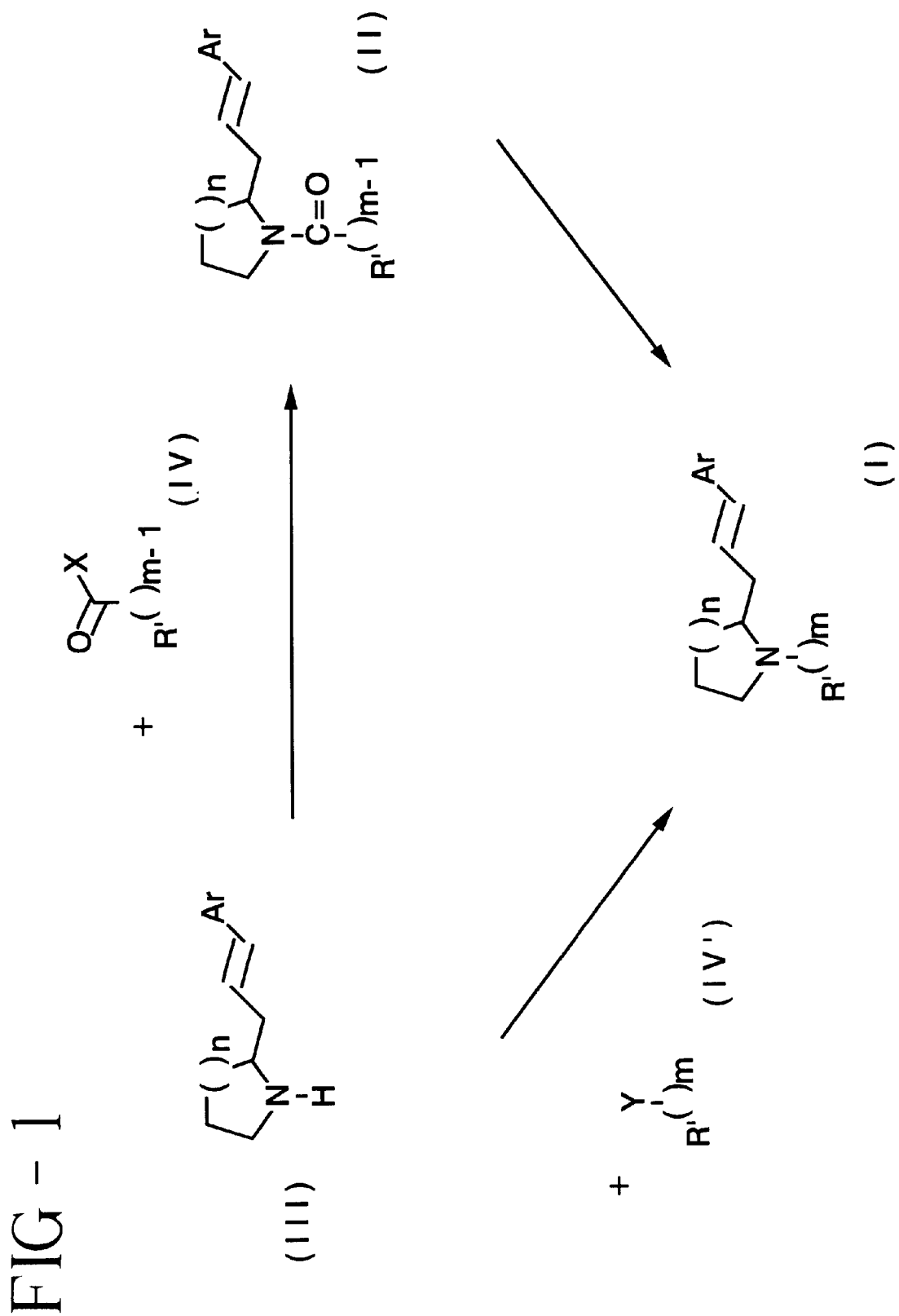
FIG. 1 is an illustration of the reaction scheme for preparing the 2-(arylalkyl)azacycloalkane compounds of the present invention.

As regards the compounds (I) of the present invention:

Aryl is understood to mean unsaturated mono- or bicyclic carbon-containing radicals such as phenyl, indenyl or naphthyl, which may be partially saturated as indanyl or tetrahydronaphthyl. The phenyl radical, optionally mono- di trisubstituted, is preferred. In this case, the substituents, which may be identical or different in the case of multiple substitution, are selected from the group consisting of halogens, the nitro is group, and low-molecular-weight alkyl, haloalkyl, alkoxy and haloalkoxy radicals, in which "low-molecular-weight" is understood to mean carbon chains comprising 1 to 4 carbon atoms.

Especially preferred is the phenyl radical, unsubstituted, or mono- or disubstituted by halogen atoms and/or by low-molecular-weight alkoxy radicals such as, preferably, methoxy radicals.

Heteroaryl is understood to mean unsaturated mono- or bicyclic radicals comprising one or two heteroatoms selected from oxygen, nitrogen and sulfur. Nitrogenous and/or sulfur-containing heterocycles are preferred, especially pyridinyl or thienyl radicals.

As regards isomers, these simultaneously comprise geometrical isomers resulting from the π bond of the arylalkenyl sequence, optical isomers resulting from the asymmetry of the carbon atom at position 2 of the azacycloalkane ring, and mixtures thereof, especially the racemic mixture.

As regards the addition salts of the compounds (I), pharmaceutically acceptable acids are understood to mean inorganic or organic acids which have been shown to be nontoxic in normal therapeutic doses. These are, as non-restrictive examples, acetic, benzenesulfonic, camphosulfonic, citric, ethanesulfonic, hydrobromic, lactic, maleic, malic, methanesulfonic, mucic, nitric, pamoic, phosphoric, salicylic, stearic, succinic, sulfuric and tartaric acid, and hydrochloric acid, which is preferred. A review of the salts acceptable in pharmaceutical practice can be found in *J. Pharm. Sci.*, Vol. 66, 1977, pp. 1–19.

In another aspect, the invention concerns a process for the preparation of the compounds (I), shown in Diagram 1, from an azacycloalkane (III)

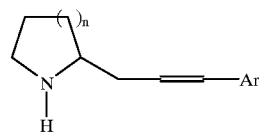

in which n and Ar are as defined for (I), by either the alkylation of an intermediate (III) with an alkyl halide (IV')

(IV')

in which m and R are as defined for (I) and Y is a halogen, preferably chlorine or bromine, or, preferably, the acylation of the intermediate (III) with a reactant (IV)

(IV)

in which m and R are as defined for (I) and X is —OH or a halogen such as chlorine or bromine, to furnish an intermediate carboxamide derivative (II)

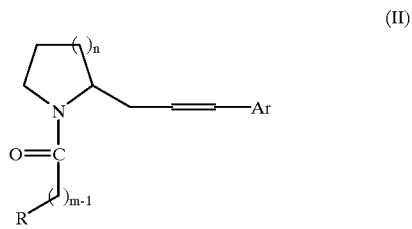

(II)

which is reduced with a metal hydride or an organometallic hydride derived from boron or preferably from aluminum.

More specifically, the process of alkylation of the intermediate (III) with the halide (IV'), which is preferably an alkyl chloride or bromide, is implemented in an inert solvent such as toluene or acetonitrile. Where appropriate, an inorganic basic agent such as sodium carbonate or an organic basic agent such as triethylamine is added to the reaction medium to promote the reaction. For 1 mol of intermediate (III) introduced, from 0.5 to 1.5 mol of alkyl halide may be used, the reaction being carried out in 2 to 3 liters of the chosen solvent. Depending on the reactants, a satisfactory result is obtained after a reaction time of 1 to 24 h at temperatures of 20 to 110° C.

The preferred process of preparation comprises, in a first step, a carboxamide (II) is obtained from the intermediate (III), and then this carboxamide is reduced with a metal hydride or an organometallic hydride; when X in the reactant (IV) is a halogen such as chlorine or bromine: The reaction is carried out in toluene or preferably methylene chloride, and comprises the addition to a solution containing 1 mol of (III) of 1.0 to 1.5 mol of an organic amine such as triethylamine, followed by the addition of the reactant (IV) in an amount equimolar to the amine. The solution is then maintained for 3 to 48 h at a temperature of between 0 and 30° C., depending on the nature of the reactants. This reaction scheme is illustrated in FIG. 1.

When X in the reactant (IV) is —OH, a suitable method comprises the preparation in situ of an anhydride of the acid, optionally mixed, following by the acylation of (III) with this anhydride. The reaction is favorably carried out in anhydrous apolar solvents of the ether-oxide class, such as tetrahydrofuran (THF), which is preferred. In an initial phase, the mixed anhydride is prepared at a temperature of between −40 and 0° C. by the addition of 1.0 to 1.5 mol of a tertiary amine such as N-methylmorpholine per mole of acid (IV), followed by 0.9 to 1.2 mole of isobutyl chloroformiate. One mole of the intermediate (III) is then added and the reaction is allowed to proceed for 1 to 48 h at a temperature of between 0 and 60° C. A satisfactory result is generally obtained after a period of 10 to 20 h with a temperature of between 10 and 25° C.

Alternative methods employ dehydrating agents. These are listed, inter alia, in March, J., *Advanced Organic Chemistry*, 3rd ed., New York: Wiley-Interscience, 1985, p. 372; those comprising the use of dicyclohexylcarbodiimide or N-N'-carbonyldiimidazole are especially suitable.

The second step, which comprises the reduction of the carboxamide (II), involves metal hydrides or organometallic hydrides derived from boron or from aluminum. Of these, one may use borane ($BH_3$) in the form of complexes and, preferably, hydrides derived from aluminum, among which there may be cited as examples simple hydrides such as $AlH_3$ or Dibal [$(CH_3)_2$—CH—$CH_2$]$_2$AlH, and mixed hydrides of aluminum and alkali metals such as sodium or lithium, the preferred reducing agents being lithium aluminum hydride ($LiAlH_4$ or LAH) and aluminum hydride $AlH_3$.

The reactions are carried out in solvents of the ether-oxide class, such as diethyl ether, 1,2-dimethoxyethane, and, more specifically, tetrahydrofuran (THF), which is especially preferred for reductions with aluminum hydride, which is the method favorably used to reduce the carboxamides (II). For this purpose, the hydride is prepared in situ from aluminum halides and metal hydrides, as described, for example, in Gaylord, N.J., ed., *Reduction with Complex Metal Hydrides*, Interscience, 1956, pp. 6–8 and 51–53.

Under the preferred conditions, the reduction in THF of 1 mol of carboxamide (II) consists first in generating the aluminum hydride in situ by reacting 0.75 to 2 mol of $AlCl_3$ with 2.2 to 6 mol of LAH, these two reactants being in a stoichiometric ratio of 1 to 3, and then in reducing (II), which is added at a temperature of between −10 and +30° C. Reaction is maintained for 1 to 24 h at the same temperature; the complexes obtained are then decomposed and the compounds of the invention (I) are isolated by suitable methods customary to a person skilled in the art. Satisfactory results are usually obtained with these reductions after 2 to 6 h of reaction at a temperature of between 10 and 20° C.

Figure 2:
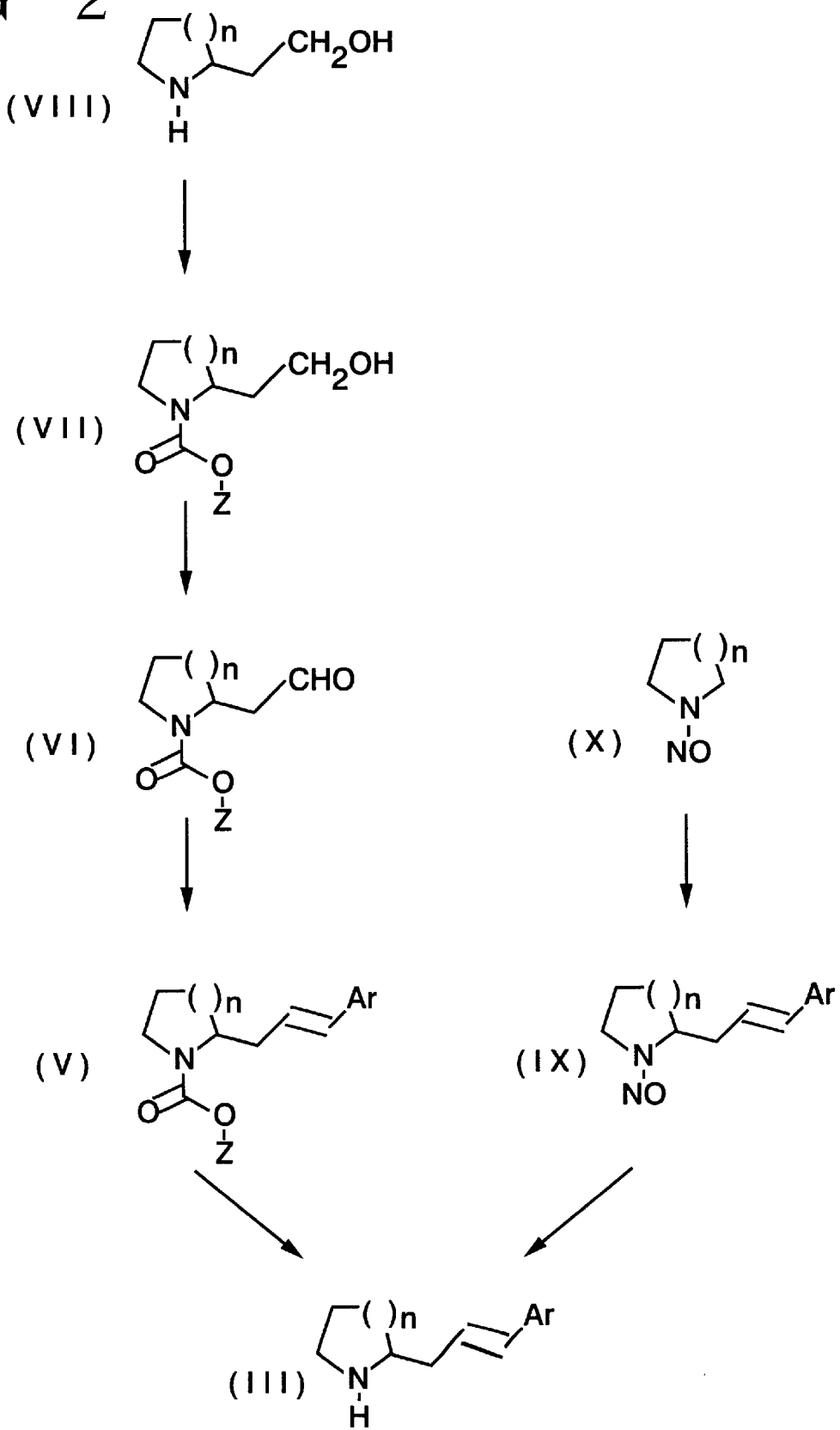
FIG. 2 is a diagram of the reaction scheme for the preparation of 2-(2-hydroxyethyl)azacycloalkanes from N-nitroso azacycloalkanes.

As described, the preparation of the compounds (I) involves the use of the essential intermediate azacycloalkanes (III), which are prepared, by methods described in or adapted from the literature, either from 2-(2-hydroxyethyl) azacycloalkanes (VIII) or from N-nitrosoazacycloalkanes (X), as shown in FIG. 2.

The process for the preparation of the azacycloalkanes (III) from the 2-(2-hydroxyethyl)azacycloalkanes (VIII), which are available commercially or are prepared according to processes of prior art, comprises, in a first step, the preparation of an intermediate carbamate (VII) in which Z is alkyl, aryl or alternatively polyalkylaryl, the t-butyl radical being, however, preferred in an N-t-butyloxycarbonyl (N-Boc) protective group. The conditions under which these processes of preparation are carried out have been amply described, for example by Geiger, R., and Koenig, W., in: Gron, E., and Meienhofer, J., *The peptides*, New York: Academic Press, 1980, Vol. 3, pp. 3–136. The preferred agent is di-tert-butyl dicarbonate, which is reacted in slight excess with compound (VIII), in solution in methylene chloride, at a temperature of between 0 and 30° C.

Controlled oxidation of the carbamate (VII) is then carried out. The reagent used for this purpose can be selected from among those described, for example, in March, J.,

*Advanced Organic Chemistry*, 3rd ed., pp. 1057–1060. The preferred reagent is pyridinium chlorochromate, which is used in an ethereal medium or in nitrobenzene, pyridine, or alternatively a halogenated hydrocarbon such as methylene chloride, which is preferred. Commonly, for 1 mole of compound (VII) to be oxidized, from 1.5 to 4 mole of pyridinium chlorochromate are used at a temperature of between 0 and 40° C. for 8 to 30 h in order to obtain the intermediate aldehyde (VI).

This compound is then subjected to a Wittig reaction with a triphenylphosphonium halide of the formula Ar—$CH_2$—P≡$(C_6H_5)_3^+$Hal, in which Ar is as defined for (I) and Hal represents a halogen such as chlorine, bromine or iodine. Different ways of using the reagents are described, as, for example, in *Organic Reactions*, Vol. 14, p. 270. They involve the use of basic reagents and may be carried out in two-phase heterogeneous media. The process used consists, however, in carrying out the reaction in an alcohol comprising up to 3 carbon atoms and in the presence of sodium alkoxide, which is formed in situ. Ethanol is preferred, and the triphenylphosphonium derivative and the alkaline agent are present in quantities close to the stoichiometric, the reaction being carried out at a temperature of between 10 and 50° C. to obtain the intermediate N-carbamyl-2-(arylalkenyl)azacycloalkane (V), which is subjected to an N-deprotection reaction, with trifluoroacetic acid, for example, in order to obtain the essential intermediate azacycloalkane (III) in the form of a mixture of Z and E isomers. These isomers are separated by conventional techniques, especially by chromatography on a silica column, as well as by selective crystallization of the hydrochloride. The Z or E isomers are identified by proton NMR, since in —$CH_a$=$CH_b$— the coupling constant between $H_a$ and $H_b$ is typically 10 Hz if the molecule is Z and approximately 17 Hz if it is E (Silverstein, R. M., et al., *Spectrometric Identification of Organic Compounds*, 4th edition, New York: Wiley, 1981, p. 235).

The alternative process for preparing the compounds (III) should be performed cautiously, especially in large-volume operations, since it involves the use of reactants and intermediates which are hazardous or have been declared potentially carcinogenic. This process comprises the alkylation of N-nitrosoazacycloalkanes (X), which are commercially available or are prepared by a nitrosation reaction of azacycloalkane, with an alkylating agent Ar—CH=CH—$CH_2$—Hal, in which the halogen is chlorine or bromine, to furnish an intermediate N-nitroso-2-(arylalkenyl)azacycloalkane (IX), which is subjected to an N-denitrosation reaction to furnish the essential intermediate (III). Within the context of the experimental description of the invention, this process is performed on small amounts according to the procedure described by Seebach, D., and Enders, D., *Chem. Ber.*, 1975, Vol. 108, pp. 1293–1320.

An optically active compound (III) may be prepared:
  by condensing a racemic compound (III) with an α-amino-acid derivative belonging to the D series or the L series and in which the amine function is protected. After deprotection, the product is separated into its diastereoisomers by chromatography; Edman degradation then yields two enantiomers of the amine (III); or alternatively,
  by dissolving a racemic compound (III) in a solution of optically active acid, for example an enantiomer of N-actylphenaylalanine, to form two diastereoisomeric salts, and then, using the difference in solubility, crystallizing out one of the salts selectively in a suitable solvent.

The present invention is illustrated non-restrictively by the examples that follow. The state of purity, the physicochemical properties and the structural identity of the products are determined and reported as follows:

The products are purified by suitable techniques, especially by column chromatography, for which the so-called "Chromatoflash" technique on a silica column (supplier: Merck; product: Kieselgel H 60, particle size 230 to 400 mesh) is favorably used. The purity of the products is determined by thin-layer chromatography (TLC) on silica (Merck ready-to-use plates); the Rf values observed and the elution solvents used are indicated in the examples.

The physicochemical properties of the products are represented by:
a) the melting point, determined by the capillary tube method, the stated value being uncorrected;
b) infrared spectrography (IR) of the compounds in KBr disks; the most intense absorption bands are reported as the value of their wavelength in $cm^{-1}$;
c) the rotatory power, determined at a temperature in the vicinity of 20° C. on a Polartronic apparatus in a cell 10 cm long;
  the structural identity of the products is determined on the basis of:
a) proton nuclear magnetic resonance (NMR) determined at 90 or 400 MHz, the products being solubilized in deuterochloroform. The appearance of the signals and their chemical shift, expressed in ppm relative to tetramethylsilane used as internal reference, are given. Protons characterized as exchangeable after the addition of deuterium oxide are also indicated;
b) elemental percentage analysis, the results of which, in accordance with the accepted norms, are not reported, but are indicated as having been performed by the listing of the element assayed;
c) high-pressure liquid chromatography on a chiral alpha AGP (α-glycoprotein) column, with UV detection at 220 nm, for assessment of optical purity.

EXAMPLES

Chemical Experimental Part

Preparation 1: (E)-(2-cinnamyl)pyrrolidine (formula III; Ar=$C_6H_5$, n=1)

Stage a) In a one-liter reactor protected from moisture and in a nitrogen atmosphere there are introduced 600 ml of THF dehydrated over molecular sieve and 25.3 g (35.0 ml–0.25 mol) of diisopropylamine. The solution is cooled to −70° C. with a dry ice/acetone mixture, and 100 ml of a 2.5 M solution (0.25 mol) of n-butyllithium in hexane are added while the temperature is maintained at α60/−50° C.

The mixture is kept stirring for 15 minutes at −35 70° C., and a solution of 25.0 g (0.25 mol) of N-nitrosopyrrolidine (formula X; n=1) in 25 ml of anhydrous THF is added during 5 min at this same temperature. The orange solution is stirred for 10 minutes, and 49.3 g (0.25 mol) of cinnamyl bromide dissolved in 50 ml of anhydrous THF are then added during 15 minutes at −70° C.

The reaction medium is maintained for 2 hours at −70° C., and then with stirring for 16 hours at −20/−25° C., after which 15.0 ml of pure acetic acid are added, causing the formation of some yellowish insoluble matter. The suspension is precipitated with stirring in 600 ml of saturated NaCl solution and 600 ml of methylene chloride. The aqueous phase is separated and extracted with 200 ml of methylene chloride. The combined organic phases are extracted with 200 ml of saturated NaCl solution and are then dehydrated over $Na_2SO_4$.

After evaporation of the solvent under vacuum and on a water bath, the residual brown oil (60.0 g) is purified by chromatography on a silica column. Elution with methylene chloride yields purified (E)-2-cinnamyl-N-nitrosopyrrolidine (formula IX; $Ar=C_6H_5$, n=1) in the form of a yellowish viscous oil.

Weight: 24.9 g Yield: 46%

TLC: Rf=0.75–0.85 (50:50 v/v hexane/ethyl acetate)

NMR: 1.80–2.40 (m, 4H); 2.40–3.20 (m, 2H); 3.30–3.90 (m, 2H); 4.25–4.70 (m, 1H); 6.00–6.60 (m, 2H); 7.10–7.50 (m, 5H).

Stage b) In a reactor protected from humidity there are introduced 24.0 g (0.111 mol) of the N-nitroso derivative obtained in Stage a) above, dissolved in 1200 ml of anhydrous diethylether. With stirring and while a temperature of 25±5° C. is maintained, the solution is saturated in the course of approximately 1 h 30 min by bubbling gaseous hydrochloric acid through it. The solution is left for 16 hours with stirring at 15–20° C., and the excess acid is then removed by bubbling with nitrogen.

The ether phase is extracted with 3×800 ml of water. The combined acidic aqueous phases are alkalinized at a temperature below 10° C. by adding sodium hydroxide solution to pH 12. The mixture is extracted with 3×750 ml of ether; the combined ether phases are washed by extractions with 3×400 ml of saturated aqueous NaCl solution and are then dried over $Na_2SO_4$. After evaporation of the ether, the crude product (13.6 g) is purified by chromatography on a silica column.

Elution with methylene chloride and then with a 92:8 v/v mixture of methylene chloride and 10% ammoniacal methanol yields the purified compound in the form of a pale yellow, viscous oil.

Weight: 9.0 g Yield: 43%

TLC: 0.35–0.45 (92:8 v/v methylene chloride/10% ammoniacal methanol)

NMR: 1.20–2.10 (m, 4H); 2.35 (t, 2H); 2.70–3.20 (m, 3H); 3.3 (s, 1H exch. $D_2O$); 6.00–6.60 (m, 2H); 7.00–7.50 (m, 5H).

Stage c) (−)(E)-(2-cinnamyl)pyrrolidine 13.5 g of (±)-(E)-(2-cinnamyl)pyrrolidine obtained in Stage a) above and 7.46 g (0.036 mmol) of N-acetyl-L-phenylalanine are dissolved in 250 ml of boiling acetone. After filtration on diatomaceous earth, the insoluble matter that precipitates upon cooling for 16 h at 20±3° C. is filtered out, then recrystallized twice in the same manner.

Treatment in an alkaline medium yields, after extraction with ether followed by evaporation, (−)-(E)-(2-cinnamyl) pyrrolidine in the form of a pale yellow oil. Weight: 2.5 g $[\alpha]_D=-12.8°$ (c=1, methylene chloride)

Stage d) (+)-(E)-(2-cinnamyl)pyrrolidine

The filtrate obtained from the first filtration of Stage c) above is treated in an alkaline medium; 9.5 g of a base with a high concentration of +enantiomer are obtained. As in the preceding stage, a diastereoisomeric salt, this time with N-acetyl-D-phenylalanine, is prepared in acetone. 2.6 g of (+)-E-2-cinnamyl pyrrolidine are obtained. $[\alpha]_D=+13.6°$ (c=1, methylene chloride)

Preparations 2

Intermediates (VI)

1°) N-t-butyloxycarbonyl-2-(2-acetaldehyde) piperidine (formula VI; n=2)

Stage 1 In a two-liter reactor protected from moisture there are introduced 40.0 g (0.309 mol) of 2-(2-hydroxyethyl) piperidine (formula VIII; n=2) in 600 ml of methylene chloride dehydrated over molecular sieve. To the pale yellow solution obtained are added rapidly 80.0 g (0.370 mol) of di-tert-butyl dicarbonate. The mixture is left stirring for one hour at 20–25° C. and then let stand for 16 h at 20° C.

The solvent is removed by distillation under vacuum and on a water bath. The residual yellow oil is purified by chromatography on a silica column. Elution with a 95:5 v/v mixture of methylene chloride and methanol furnishes N-t-butyloxycarbonyl-2-(2-hydroxyethyl)piperidine (formula VII; Z=t-butyl, n=2).

Weight: 66.7 g Yield: 94%

TLC: Rf=0.70–0.80 (90:10 v/v ethyl acetate/hexane)

NMR: 1.20–2.20 (m, 18H); 2.50–3.00 (m, 1H); 3.20–3.80 (m, 2H); 3.80–4.50 (m, 2H).

Stage 2 In a 3-liter reactor protected from moisture, 66.0 g (0.287 mol) of the N-protected alcohol obtained in Stage 1 above are dissolved in 2.4 liters of anhydrous methylene chloride. 125.0 g (0.58 mol) of pyridinium chlorochromate are added to the solution. The orange suspension, which rapidly turns blackish, is maintained at 20±3° C., with stirring, for 16 h.

Thereafter, once settling has taken place the organic phase is separated and is extracted with 1 liter of 1 N NaOH solution. The emulsified mixture is filtered through a Buchner funnel lined with diatomaceous earth. The filtrate is allowed to settle and the aqueous phase is decanted and discarded. The organic phase is dehydrated over $Na_2SO_4$ and the solvent is then removed by distillation. The blackish residue (35.0 g) is purified by chromatography on a silica column. Elution with ethyl acetate yields N-t-butyloxycarbonyl-2-(2-acetaldehyde)piperidine (formula VI; Z=t-butyl, n=2).

Weight: 16.2 g Yield: 25%

TLC: Rf=0.50–0.60 (50:50 v/v methylene chloride/diethyl ether)

NMR: 1.20–2.00 (m, 15H); 2.35–3.00 (m, 3H); 3.80–4.20 (m, 1H); 4.70–5.00 (m, 1H); 9.70–9.80 (m, 1H)

2°) N-t-butyloxycarbonyl-2-(2-acetaldehyde) pyrrolidine (formula VI; n=1)

Stage 1 N-Boc-2-pyrrolidine methanol

The compound is prepared as described in §1°), Stage 1 above, from 2-pyrrolidine ethanol, with a yield of 100%.

TLC: Rf=0.70–0.85 (95:15 v/v ethyl acetate/hexane)

Stage 2 N-Boc-2-pyrrolidine methanal

The compound is prepared from the N-protected alcohol obtained in Stage 1 above, according to the procedure described in §1°), Stage 2, with a yield of 68%.

TLC: Rf=0.85–0.95 (80:20 v/v ethyl acetate/hexane)

Stage 3: N-Boc-2-(2-methoxyethenyl)pyrrolidine

In a reactor protected from moisture, there are placed 895 ml of absolute ethanol, followed, with stirring, by 11.8 g (0.510 mol) of scraped sodium. After dissolution, at 20–25° C., 174.7 g of (methoxymethyl)triphenylphosphonium chloride are added. The white suspension is stirred for 30 min at 20–25° C., and a solution of 71 g (0.356 mol) of the aldehyde obtained in Stage 2 above in 199 ml of absolute ethanol is then introduced. The reaction medium is kept boiling for 2 h 30 min and is then cooled and evaporated under vacuum and on a water bath. The orange residue is dissolved in pentane and then filtered. The filtrate is concentrated and chromatographed on silica, with elution by means of an 85:15 v/v mixture of hexane and ethyl acetate.

Weight=60 g Yield=74%

TLC: Rf=0.75–0.90 (70:30 v/v hexane/ethyl acetate)

Stage 4: In a reactor there are introduced one liter of tetrahydrofuran and 102 g of the vinyl ether obtained in the preceding stage, followed by 150 ml of 10% (w/v) hydrochloric acid. The brown solution is kept stirring at 40° C. for 30 min and then cooled. One liter of ether is added and, after settling has taken place, the organic phase is separated, washed with a saturated NaCl solution, and then evaporated. The brown residue is purified by the Chromatoflash technique on silica, with elution by means of a 75:25 v/v mixture of hexane and methyl acetate.

Weight: 71.9 g Yield: 75%

Preparation 2A: (Z)- and (E)-(2-cinnamyl) piperidine (formula III; Ar=$C_6H_5$, n=2)

Stage a) In a reactor protected from moisture, there are introduced 180 ml of absolute ethanol, followed, with stirring, by 1.63 g (0.071 mol) of scraped sodium. After dissolution, at 20–25° C., 27.3 g (0.071 mol) of benzyltriphenylphosphonium chloride are added. The yellowish suspension is kept stirring for 30 min at 20–25° C. and a solution of 16.0 g (0.070 mol) of the previously obtained acetaldehyde (formula VI; n=2) in 35 ml of absolute ethanol is then introduced during approximately 2 min. The white solution obtained is maintained for 30 minutes at 20–25° C. and the insoluble matter is filtered out on a Buchner funnel and discarded. The filtrate is evaporated under vacuum and on a water bath. The oily residue is solidified in 500 ml of n-pentane, and this new insoluble matter is filtered out and removed. The filtrate is concentrated. 19.0 g of crude N-t-butyloxycarbonyl-(2-cinnamyl)piperidine are obtained (formula V; Z=t-butyl, Ar=$C_6H_5$, n=2) (yield =90%) and are introduced in the next stage without further treatment.

Stage b) In a reactor protected from moisture, 19.0 g (0.063 mol) of the compound (V) obtained in the preceding stage are dissolved in 400 ml of anhydrous methylene chloride. The solution is cooled with an ice bath, and 190 ml of pure trifluoroacetic acid are added with stirring over a period of 10 minutes at a temperature below 5° C. The solution is maintained at this temperature for 30 minutes and is then concentrated under vacuum and on a water bath. The residue is dissolved in 600 ml of ether and extracted with 200 ml of 1 N NaOH solution. The ether phase is washed with water and then dried over $Na_2SO_4$.

The ether is evaporated and the crude product (12.0 g) is obtained in the form of a light brown oil, which is dissolved in 120 ml of anhydrous methylene chloride. To this solution are added 25 ml of 5 N ethereal hydrogen chloride and the solvents are then evaporated by distillation. The residue is dissolved in 150 ml of boiling isopropanol. The insoluble matter which precipitates on cooling with stirring is filtered out on a Buchner and then recrystallized in absolute ethanol. After removal of the residual solvents under vacuum, (E)-(2-cinnamyl)piperidine hydrochloride is obtained (formula III-E; Ar=$C_6H_5$, n=2).

Weight: 4.6 g Yield: 30.7% mp: 225° C.

TLC: Rf=0.30–0.40 (90:10 v/v methylene chloride/10% ammoniacal methanol)

Analysis ($C_{14}H_{20}ClN$): % C, H, Cl, N in agreement.

Treatment of 4.0 g (16.8 mmol) of the hydrochloride in an alkaline medium and extraction with ether followed by evaporation yields 3.3 g of (E)-(2-cinnamyl)piperidine in the form of a pale yellow, viscous oil.

NMR: 1.00–1.90 (m, 6H); 1.95 (s, 1H exch. $D_2O$); 2.10–2.40 (m, 2H); 2.40–2.80 (m, 2H); 2.90–3.20 (m, 1H); 6.00–6.60 (m, 2H); 7.10–7.45 (m, 5H).

The previously obtained isopropanol-containing filtrate is concentrated by distillation. The residue (9.0 g) is treated and extracted in an alkaline medium with ether. The ether is removed and the oily residue (6.4 g) purified by chromatography on a silica column. Elution with a 95:5 v/v mixture of methylene chloride and 10% ammoniacal methanol yields pure (Z)-(2-cinnamyl)piperidine (formula III-Z; Ar=$C_6H_5$, n=2) in the form of a highly viscous oil which solidifies slowly in the cold state.

Weight: 3.0 g Yield: 23.7%

TLC: Rf=0.40–0.50 (90:10 v/v methylene chloride/10% ammoniacal methanol)

NMR: 1.00–1.90 (m, 6H); 2.20 (s, 1H exch. $D_2O$); 2.30–2.80 (m, 4H); 2.90–3.20 (m, 1H); 5.50–5.85 (m, 1H); 6.40–6.60 (m, 1H); 7.10–7.40 (m, 5H);

Stage c) (−)-(E)-(2-cinnamyl)piperidine

From (±)-(E)-(2-cinnamyl)piperidine obtained in the preceding stage, according to a method similar to Preparation 1, Stage c), in which the last recrystallization is carried out in an aqueous medium, there is obtained (−)-(E)-(2-cinnamyl) piperidine in the form of an oil, with a yield of 33%. $[\alpha]_D$=−8.1° (c=2, methylene chloride)

Stage d) (+)-(E)-(2-cinnamyl)piperidine

According to the process described for Preparation 1, Stage d), the last recrystallization being performed in an aqueous medium, (+)-(E)-(2-cinnamyl)piperidine is obtained with a yield of 30% after return to the base. $[\alpha]_D$=+8.1° (c=2, methylene chloride)

Preparation 2B: (Z)- and (E)-2-(p-fluorocinnamyl) piperidine (formula III; Ar=p-fluorophenyl, n=2)

Stage a) According to the method of Preparation 2A, Stage a), from p-fluorobenzyl triphenylphosphonium there is obtained N-t-butyloxycarbonyl-2-(p-fluorocinnamyl) piperidine in the form of a yellow oil with a yield of 96%.

Stage b) Deprotection with trifluoroacetic acid is performed according to the method of Preparation 2A, Stage b). The crude product obtained in the form of an orangish-yellow oil is a mixture of the Z and E isomers which is separated by the Chromatoflash technique on a silica column. Elution with a mixture of methylene chloride and 10% ammoniacal methanol in a v/v ratio of 95:5, followed by 90:10, furnishes different fractions in succession. To the least polar fractions, dissolved in methylene chloride, is added 5 N ethereal hydrogen chloride; the solvents are then evaporated and the residue is dissolved in isopropanol and solidified, with stirring, by the addition of ether. A white precipitate of (Z)-2-(p-fluorocinnamyl)piperidine hydrochloride is obtained. mp=135° C.

Treatment in an alkaline medium, extraction with ether and evaporation furnishes (Z)-2-(p-fluorocinnamyl) piperidine in the form of a yellow oil. Yield: 13%

TLC: Rf=0.70–0.85 (80:20 v/v methylene chloride/10% ammoniacal methanol)

Comparable treatment of the most polar fractions yields (E)-2-(p-fluorocinnamyl)piperidine in the form of a white precipitate.

mp=193° C. (isopropanol)

Return to the base furnishes (E)-2-(p-fluorocinnamyl) piperidine with a yield of 25%.

TLC: RF=0.60–0.75 (80:20 v/v methylene chloride/10% ammoniacal methanol)

Preparation 2C: (E)-2-(p-chlorocinnamyl)piperidine (formula III; Ar=p-chlorophenyl, n=2)

Stage a) According to the method of Preparation 2A, Stage a), from p-chlorobenzyl triphenylphosponium, there is obtained N-t-butyloxycarbonyl-2-(p-chlorocinnamyl) piperidine in the form of a yellow oil with a yield of 94%.

Stage b) Deprotection with trifluoroacetic acid is performed according to the method of Preparation 2A, Stage b). The product, obtained in the form of a yellow oil, is a mixture of the Z and E isomers. Elution with a 90:10 v/v mixture of methylene chloride and 10% methanol by the Chromatoflash technique on silica furnishes (E)-2-(p-chlorocinnamyl) piperidine in the form of a pale yellow oil with a yield of 24%.

Preparation 2D: (E)-2-(m-chlorocinnamyl)piperidine (formula III; Ar=p-chlorophenyl, n=2)

Stage a) According to a method similar to that of Preparation 2A, Stage a), from m-chlorobenzyl triphenylphosponium there is obtained N-t-butyloxycarbonyl-2-(m-chlorocinnamyl)piperidine with a yield of 99%.

Stage b) Deprotection with trifluoroacetic acid is carried out according to the method of Preparation 2A, Stage b). The product obtained is a mixture of the Z and E isomers. Elution with a 90:10 v/v mixture of methylene chloride and 10% ammoniacal methanol by the Chromatoflash technique on silica furnishes the E isomer in the most polar fractions. The intermediate fractions are chromatographed a second time under the same conditions. All of the fractions with a high E-isomer content are combined, and, as described with regard to Preparation 2B, Stage b), are converted to the hydrochloride, which is recrystallized in isopropanol, then treated in an alkaline medium, extracted with ether and concentrated to furnish (E)-2-(m-chlorocinnamyl)piperidine with a yield of 24%.

Preparation 2E: (E)-2-(3,4-dichloro)cinnamyl piperidine (formula III; Ar=3,4-dichlorophenyl, n=2)

Stage a) According to Method 2A, Stage a), from 3,4-dichlorobenzyl triphenylphosphonium chloride there is obtained N-t-butyloxycarbonyl-2-(3,4-dichloro)cinnamyl piperidine in the form of a yellow oil. Yield: 91%.

TLC: Rf=0.60–0.80 (methylene chloride)

Stage b) Deprotection with trifluoroacetic acid and separation of the E isomer are performed according to the method described for Stage b) of Preparation 2D. (E)- 2-(3,4-dichloro)cinnamyl piperidine is obtained in the form of a yellow oil with a yield of 18%.

TLC: Rf=0.35–0.55 (90:10 v/v methylene chloride/10% ammoniacal MeOH)

Preparation 2F: (E)-2-(p-methylcinnamyl)piperidine (formula III; Ar=p-toluyl, n=2)

Stage a) According to Method 2A, Stage a), from p-methylbenzyltriphenyl phosphonium, there is obtained N-t-butyloxycarbonyl-2-(p-methylcinnamyl)piperidine (formula V; Ar =p-toluyl, n=2) in the form of an orangish-yellow oil. Yield: 98%

TLC: Rf=0.25–0.55 (methylene chloride)

Stage b) The intermediate V from the preceding stage is deprotected and the E isomer is separated according to the method of Preparation 2D, Stage b). (E)-2-(p-methylcinnamyl)piperidine is obtained in the form of a yellow oil with a yield of 14%. The corresponding hydrochloride is a white solid with a melting point of 178° C. (isopropanol).

Preparation 2G: (E)-2-(p-trifluoromethylcinnamyl) piperidine (formula III; Ar=p-trifluoromethylphenyl, n=2)

Stage a) According to Method 2A, Stage a), from p-trifluoromethylbenzyltriphenyl phosphonium there is obtained N-Boc-2-(p-trifluoromethylcinnamyl)piperidine (formula V; Ar=p-trifluoromethylphenyl, n=2) in the form of a yellow oil. Yield: 94%

Stage b) The intermediate V from the preceding stage is deprotected and the E isomer is separated according to the method of Preparation 2B, Stage b), applied to the E isomer. (E)-2-(p-trifluoromethylcinnamyl)piperidine is obtained with a yield of 17%.

Preparation 2H: (E)-2-(p-methoxycinnamyl) piperidine (formula III; Ar=p-methoxyphenyl, n=2)

Stage a) According to Process 2A, Stage a), from p-methoxybenzyltriphenyl phosphonium chloride, N-Boc-2-(p-methoxycinnamyl)piperidine (formula V; Ar=p-methoxyphenyl, n=2) is obtained in the form of a yellow oil and is purified by chromatography on a silica column, with elution by means of a 98:2 v/v mixture of methylene chloride and acetone. Yield: 94%.

TLC: Rf=0.55–0.75 (98:2 v/v methylene chloride/acetone)

Stage b) Intermediate V from the preceding stage is deprotected and the E isomer is purified according to Process 2D, Stage b). (E)-2-(p-methoxycinnamyl)piperidine is obtained in the form of a yellow oil with a yield of 15%.

TLC: Rf=0.45–0.70 (90:10 v/v methylene chloride/10% ammoniacal MeOH).

Preparation 2I: (E)-2-(1-naphth-1-yl-propen-3-yl) piperidine (formula III; Ar=naphth-1-yl, n=2)

Stage a) According to Process 2A, Stage a), from naphth-1-yl-methyltriphenyl phosponium there is obtained N-Boc-2-(1-naphth-1-yl-propen-3-yl)piperidine (formula V; Ar=naphth-1-yl, n=2) with a yield of 79%.

Stage b) Intermediate V from the preceding stage is deprotected and the E isomer is separated according to a method similar to that of Preparation 2B, Stage b). (E)-2-(1-naphth-1-yl-propen-3-yl)piperidine is obtained with a yield of 19%.

Preparation 2J: (E)-2-(1-thien-2-yl-propen-3-yl) piperidine (formula III; Ar=thien-2-yl, n=2)

Stage a) According to a method similar to that of Preparation 2A, Stage a), from thien-2-yl-methyltriphenyl phosponium chloride there is obtained N-Boc-2-(1-thien-2-yl-propen-3-yl) piperidine with a yield of 91%.

Stage b) Deprotection is carried out according to Process 2B, Stage b). (E)-2-(1-thien-2-yl-propen-3-yl)piperidine is obtained with a yield of 5%.

Preparation 2K: (Z)-2-(cinnamyl)pyrrolidine (formula III-Z; Ar=$C_6H_5$, n=1)

Stage a) In a reactor protected from moisture, there are introduced 235 ml of absolute ethanol, followed, with stirring, by 2.16 g (0.094 mol) of scraped sodium. After dissolution, at 20–25° C., 36.5 g (0.094 mol) of benzyltriphenyl phosphonium chloride are added. The yellow solution is kept stirring for 30 min, after which a solution of 20 g (0.094 mol) of the previously obtained acetaldehyde (formula VI; n=1) in 47 ml of absolute ethanol is introduced during approximately 2 min. The white suspension is kept stirring for 45 min at 20–25° C., and the insoluble matter is then filtered out on a Buchner and discarded. The filtrate is evaporated under vacuum and on a water bath. The oily residue, dissolved in 300 ml of pentane, is maintained at 0°C. for 2 h with stirring, and is then filtered and concentrated. This last step is repeated. The product is 24.5 g (yield=91%) of crude N-Boc-2-(cinnamyl)pyrrolidine (formula V; Ar=$C_6H_5$, n=1) in the form of a yellow oil, which is introduced in the next stage without further treatment.

Stage b) The intermediate V from the preceding stage is deprotected and the Z isomer is separated according to a method similar to that of Preparation 2D, Stage b). (Z)-2-(cinnamyl)pyrrolidine is obtained with a yield of 28%.

TLC: Rf=0.35–0.50 (90:10 v/v methylene chloride/10% ammoniacal MeOH)

Preparation 2L: (E)-2-(p-fluorocinnamyl)pyrrolidine
(formula III; Ar=p-fluorophenyl, n=1)

Stage a) In a reactor protected from moisture there are introduced 42 g (0.103 mol) of p-fluorobenzyltriphenyl phosphonium chloride in 235 ml of toluene dehydrated on molecular sieve. 60 ml of a 2.5 M solution of n-butyllithium in hexane are then introduced during 10 min. The red suspension is kept stirring for 2 h at 20–25° C., after which 20 g (0.094 mol) of the previously obtained acetaldehyde (formula VI; n=1) in 42.2 ml of toluene are introduced. The dark red suspension obtained is kept stirring for 16 h, after which 80 ml of a saturated ammonium chloride solution are introduced with cooling to 20° C. After 15 min of stirring, the insoluble matter is filtered out and discarded. After settling has taken place, the toluene phase of the filtrate is separated, dried over $Na_2SO_4$ and evaporated. The oily brown residue is solidified in 300 ml of n-pentane, and the new insoluble matter is filtered out and removed; the filtrate is concentrated. This last purification step is repeated. 23.6 g (yield: 82%) of crude N-Boc-2-(p-fluorocinnamyl) pyrrolidine are obtained (formula V; Ar=p-fluorophenyl, n=1) in the form of an orange oil.

Stage b) Deprotection with trifluoroacetic acid and separation of the E isomer are carried out according to the method of Preparation 2B, Stage b) applied to the E isomer, with recrystallization in ethyl acetate. (E)-2-(p-fluorocinnamyl) pyrrolidine hydrochloride is obtained in the form of a white precipitate. Return to the base furnishes (E)-2-(p-fluorocinnamyl)pyrrolidine with a yield of 19%.

TLC: Rf=0.30–0.50 (90:10 v/v methylene chloride/10% ammoniacal MeOH)

Example 1.1: (+)-(E)-2-cinnamyl-1-cyclopropylmethylpyrrolidine (formula I; Ar=$C_6H_5$, m=1, n=1, R=cyclopropyl)

Stage a) In a reactor protected from moisture, there are introduced 4.5 g (0.024 mol) of (E)-2-(cinnamyl)pyrrolidine (Preparation 1, Stage b) dissolved in 100 ml of methylene chloride dehydrated over molecular sieve. 2.5 g (3.5 ml–0.025 mol) of triethylamine are added with stirring, followed by 2.5 g (2.2 ml–0.024 mol) of cyclopropanecarboxylic acid chloride (formula IV; m=1, R=cyclopropyl) at a temperature below 10° C. during approximately 10 min. The brown solution is kept stirring for 1 h and the mixture is extracted successively with:

30 ml of 10% ammonia solution followed by 30 ml of water, 30 ml of 10% HCl solution followed by 30 ml of water, 30 ml of saturated $NaHCO_3$ solution followed by 30 ml of water.

The organic phase is dehydrated over $Na_2SO_4$ and the solvent is then evaporated under vacuum and on a water bath. The oily residue (5.9 g) is purified by chromatography on a silica column. Elution with a 95:5 v/v mixture of methylene chloride and acetone yields pure 2-cinnamyl-1-cyclopropanecarbonylpyrrolidine (formula II; Ar=$C_6H_5$, m=1, n=1, R=cyclopropyl) in the form of a yellow oil.

Weight: 4.2 g Yield: 65.8%

TLC: Rf=0.35–0.45 (95:5 v/v methylene chloride/acetone)

NMR: 0.60–1.20 (m, 4H); 1.40–2.05 (m, 5H); 2.10–2.90 (m, 2H); 3.40–3.75 (m, 2H); 4.00–4.35 (m, 1H); 5.85–6.60 (m, 2H); 7.10–7.50 (m, 5H).

Stage b) In a nitrogen atmosphere, under protection from moisture and without exceeding 0° C., there are prepared, on the one hand, a suspension of 1.9 g (0.049 mol) of lithium aluminum hydride (LAH) in 25 ml of THF dehydrated on molecular sieve, and on the other hand, a solution of 2.15 g (0.016 mol) of aluminum chloride in 25 ml of diethyl ether, also dehydrated on sieve.

After 30 min of contact for each preparation, the LAH/THF suspension is added to the ethereal $AlCl_3$ solution during 10 min at 0° C., and a solution of 4.0 g (0.016 mol) of the amide (II) obtained in the preceding stage in 16 ml of anhydrous THF is then added at this temperature and during 10 minutes. After 30 minutes at 0° C., the mixture is brought to reflux for 10 min and is then cooled rapidly to OOC. There are then added, dropwise and cautiously, 2.9 ml of 15% (w/v) NaOH solution followed by 3.6 ml of water. After 30 minutes of contact, the mixture is filtered through a Buchner funnel lined with a bed of diatomaceous earth. The filtrate is concentrated under vacuum and on a water bath to yield (E)-2-cinnamyl-N-cyclopropylmethylpyrrolidine, which is shown to be pure by TLC.

Weight: 3.2 g Yield: 84.6%

TLC: Rf=0.55–0.75 (95:5 v/v methylene chloride/acetone)

NMR: 0.00–0.30 (m, 2H); 0.40–0.70 (m, 2H); 0.80–1.20 (m, 1H); 1.40–3.00 (m, 10H); 3.20–3.50 (m, 1H); 6.00–6.60 (m, 2H); 7.10–7.55 (m, 5H).

Hydrochloride: The base is dissolved in 50 ml of methylene chloride, 5 ml of 5 N ethereal hydrogen chloride are added and the solvents are removed by distillation. The solid residue is crystallized by dissolution in 50 ml of ethyl acetate. The white insoluble matter is filtered out and dried under vacuum to constant weight. mp=163° C.

Analysis ($C_{17}H_{24}ClN$): % C, H, Cl, N in agreement

IR (KBr): 2950, 2500, 1460, 1440, 1050, 1020, 970, 940, 830, 740, 690 $cm^{-1}$.

Example 1.2: (+)-(E)-2-cinnamyl-1-cyclopropylmethylpyrrolidine (formula I; Ar=$C_6H_5$, m=1, n=1, R=cyclopropyl)

The compound is prepared as described in Example 1.1 above, from (−)-(E)-2-(cinnamyl)pyrrolidine (Preparation 1, Stage c).

Stage a) (+)-(E)-2-cinnamyl-1-cyclopropanecarbonylpyrrolidine ( II; Ar=$C_6H_5$, m=1, n=1, R=cyclopropyl) Yield: 100% $[\alpha]_D$=24.5° (c=1, methylene chloride)

TLC: Rf=0.35–0.50 (95:5 v/v methylene chloride/acetone)

Stage b) (+)-(E)-2-cinnamyl-1-cyclopropylmethylpyrrolidine Yield: 96% $[\alpha]_D$=91.9° (c=1, methylene chloride)

TLC: Rf=0.45–0.60 (95:5 v/v methylene chloride/10% ammoniacal MeOH)

NMR: Same as for the racemic compound (Ex. 1.1).

Hydrochloride: mp=196–198° C. (isopropanol).

Analysis ($C_{17}H_{21}ClN$): % C, H, N in agreement.

IR (KBr): Same as for the racemic compound (Ex. 1.1).

Example 1.3: (−)-(E)-2-cinnamyl-1-cyclopropylmethylpyrrolidine (formula I; Ar=$C_6H_5$, m=1, n=1, R=cyclopropyl)

The compound is prepared as described in Example 1.1 above, from (+)-(E)-2-(cinnamyl)pyrrolidine (Preparation 1, Stage d).

Stage a) (−)-(E)-2-cinnamyl-1-cyclopropanecarbonylpyrrolidine (formula II; Ar=$C_6H_5$, m=1, n=1, R=cyclopropyl) Yield: 100% $[\alpha]_D$=−20.8° (c=1, methylene chloride)

TLC: Rf=0.35–0.50 (95:5 v/v methylene chloride/acetone)

Stage b) (−)-(E)-2-cinnamyl-1-cyclopropylmethylpyrrolidine Yield: 94% [α]$_D$=+91.8° (C=1, methylene chloride)

TLC: Rf=0.45–0.60 (95:5 v/v methylene chloride/10% ammoniacal MeOH)

NMR: Same as for the racemic compound (Ex. 1.1).
Hydrochloride: mp=196–198° C. (isopropanol).
Analysis ($C_{17}H_{24}ClN$): % C, H, N in agreement.
IR: Same as for the racemic compound (Ex. 1.1).

Example 1.4: (E)-2-cinnamyl-1-cyclobutylmethylpyrrolidine (formula I; Ar=$C_6H_5$, m=1, n=1, R=cyclobutyl)

Stage a) According to the method of Example 1.1, Stage a), from 2-(cinnamyl)pyrrolidine and cyclobutanecarboxylic acid chloride there is obtained, with a yield of 95%, 2-cinnamyl-1-cyclobutanecarbonylpyrrolidine (formula II; Ar=$C_6H_5$, m=1, n=1, R=cyclobutyl), which is introduced in the next stage without further treatment.

Stage b) Reduction performed according to the method of Example 1.1, Stage b), with LAH-AlCl$_3$, results in 2-cinnamyl-1-cyclobutylmethylpyrrolidine with a yield of 45%.

TLC: Rf=0.50–0.60 (95:5 v/v methylene chloride/10% ammoniacal MeOH)
NMR: 1.40–3.20 (m, 18H); 5.95–6.95 (m, 2H); 7.00–7.45 (m, 5H).
Hydrochloride: The compound, prepared as described in Example 1.1, is crystallized in a methylene chloride/ethyl ether mixture. mp=170–171° C.
Analysis ($C_{18}H_{26}ClN$): % C, H, Cl, N in agreement.
IR (KBr): 2950, 2500, 1440, 1240, 1020, 970, 740, 680 cm$^{-1}$.

Example 1.5: (E)-2-cinnamyl-1-cyclopropylethylpyrrolidine (formula I; Ar=$C_6H_5$, m=2, n=1, R=cyclopropyl)

Stage a) In a reactor protected against moisture, there are introduced 1 g (0.010 mol) of cyclopropaneacetic acid, 2.34 g (0.012 mol) of (E)-2-(cinnamyl)pyrrolidine dissolved in 80 ml of methylene chloride dehydrated over molecular sieve and 2.9 g (0.015 mol) of 1-(3-dimethylaminopropyl)-3-ethylcarbodiimide hydrochloride. The brown solution is kept stirring for 16 h at 20–25° C. and the mixture is extracted successively with:

50 ml of 1 N HCl solution followed by 2×50 ml of water,
50 ml of saturated NaHCO$_3$ solution followed by 2×50 ml of water.

The organic phase is dehydrated over Na$_2$SO$_4$ and filtered, and the solvent is then evaporated under vacuum and on a water bath.

2-cinnamyl-1-cyclopropaneacetylpyrrolidine (formula II; Ar=$C_6H_5$, m=2, n=1, R=cyclopropyl) is obtained in the form of a brown oil. Weight=2.2 g Yield=82%

TLC: Rf=0.85–0.95 (92:8 v/v methylene chloride/10% ammoniacal MeOH)

Stage b) Amide II from the preceding stage is reduced according to the method described in Example 1.1, Stage b), followed by a purification step by chromatography on a silica column. Elution with a 90:10 v/v mixture of methylene chloride and 10% ammoniacal methanol mixture yields (E)-2-cinnamyl-1-(cyclopropylethyl)pyrrolidine in the form of a yellow oil.

Weight: 1.7 g Yield: 81%
- TLC: Rf=0.85–1.00 (90:10 v/v methylene chloride/10% ammoniacal MeOH)

NMR: 0–0.10 (m, 2H); 0.40–0.50 (m, 2H); 0.70–0.80 (m, 1H); 1.30–1.90 (m, 7H); 2.10–2.30 (m, 2H); 2.30–2.40 (m, 1H); 2.50–2.60 (m, 1H); 2.90–3.00 (m, 1H); 3.10–3.20 (m, 1H); 6.10–6.20 (m, 1H); 6.45 (d, 1H); 7.10–7.40 (m, 5H)
Hydrochloride: mp=188° C. (isopropanol)
Analysis ($CH_{18}H_{26}ClN$): % C, H, Cl, N in agreement.
IR: 2900, 2400, 1420, 1020, 960, 900, 740, 700 cm$^{-1}$.

Example 1.6: (E)-2-cinnamyl-1-phenethylpyrrolidine (formula I; Ar=$C_6H_5$, m=2, n=1, R=$C_6H_5$)

Stage a) The procedure is the same as that of Example 1.1, Stage a), the initial reactants being (E)-2-cinnamylpyrrolidine and phenylacetic acid chloride. (E)-2-cinnamyl-1-phenylacetylpyrrolidine is obtained with a yield of 97% and is introduced in the next stage without further treatment.

Stage b) Reduction according to the method of Example 1.5, Stage b) furnishes (E)-2-cinnamyl-1-(phenethyl)pyrrolidine with a yield of 45%.

TLC: Rf=0.80–0.95 (90:10 v/v methylene chloride/10% ammoniacal MeOH)
NMR: 1.50–2.00 (m, 4H); 2.10–2.30 (m, 2H); 2.30–2.60 (m, 3H); 2.70–2.90 (m, 2H); 3.00–3.20 (m, 1H); 3.20–3.30 (m, 1H); 6.10–6.20 (m, 1H); 6.45 (d, 1H); 7.10–7.40 (m, 10H).
Hydrochloride: (mp=120–122° C. (ethyl acetate/ethyl ether).
Analysis ($C_{21}H_{26}ClN$): % C, H, Cl, N in agreement.
IR (KBr): 2900; 2450; 1600; 1490; 1450; 1050; 990; 740; 690 cm$^{-1}$.

Example 2A.1: (E)-2-cinnamyl-1-cyclopropylmethylpiperidine (formula I; Ar=$C_6H_5$, m=1, n=2, R=cyclopropyl).

Stage a) The method is the same as that of Example 1.1, Stage a), the initial reactants being (E)-2-(cinnamyl)piperidine (Preparation 2A, Stage b) and cyclopropanecarboxylic acid chloride, yielding (E)-2-cinnamyl-1-cyclopropanecarbonylpiperidine (formula II; Ar=$C_6H_5$, m=1, n=2, R=cyclopropyl). Yield: 95%.

TLC: Rf=0.80–0.90 (ethyl acetate)
NMR: 0.50–1.10 (m, 5H); 1.30–1.90 (m, 8H); 4.00–5.00 (m, 1H); 5.90–60 (m, 2H); 7.10–7.40 (m, 5H).

Stage b) Amide (II) from the preceding stage is reduced as described in Example 1.1, Stage b) to yield (E)-2-cinnamyl-1-cyclopropranecarbonylpiperidine. Yield: 86%

TLC: Rf=0.65–0.80 (95:5 v/v methylene chloride/10% ammoniacal MeOH)
NMR: 0.10–0.20 (m, 2H); 0.20–0.60 (m, 2H); 0.60–1.00 (m, 1H); 1.10–1.80 (m, 6H); 2.10–2.80 (m, 6H); 2.60–3.20 (m, 1H); 5.95–6.55 (m, 2H); 7.10–7.40 (m, 5H).
Hydrochloride: The compound is prepared under the conditions described in Example 1.1, the crystallization being carried out in boiling ethyl acetate. mp=152° C.
Analysis ($C_{18}H_{26}ClN$): % C, H, Cl, N in agreement;
IR(KBr): 2950, 2680, 2500, 1440, 1360, 1260, 1200, 1120, 1020, 980, 980, 950, 820, 800, 770, 740, 680 cm$^{-1}$.

Example 2A.2: (+)-(E)-2-cinnamyl-1-(cyclopropylmethyl)piperidine (formula I; Ar=$C_6H_5$, m=1, n=2, R=cyclopropyl)

The compound is prepared as described in Example 2A.1 above, from (−)-(E)-2-(cinnamyl)piperidine (Preparation 2A, Stage c).

Stage a) (−)-(E)-2-cinnamyl-1-(cyclopropane) carbonylpiperidine (formula II; Ar=$C_6H_5$, m=1, n=2, R=cyclopropyl) Yield: 100% [α]$_D$=−6.40° (c=4, methylene chloride)

TLC: Rf=0.60–0.75 (95:5 v/v methylene chloride/acetone)

Stage b) (+)-(E)-2-cinnamyl-1-(cyclopropylmethyl) piperidine Yield: 95% $[\alpha]_D=+27.7°$ (c=1, methylene chloride)

TLC: 0.60–0.75 (95:5 v/v methylene chloride/acetone)

NMR: Same as for the racemic compound (Ex. 2A.1)

Hydrochloride: mp=153° C. (ethyl acetate).

Analysis ($C_{18}H_{26}ClN$): % C, H, Cl, N in agreement;

IR (KBr): Same as for the racemic compound (Ex. 2A.1)

Example 2A.3: (−)-(E)-2-(cinnamyl) cyclopropylmethylpiperidine (formula I; Ar=$C_6H_5$, m=1, n=2, R=cyclopropyl) The compound is prepared as described in Example 2A.1 above, from (+)-(E)-2-(cinnamyl)piperidine (Preparation 2A, Stage d).

Stage a) (+)-(E)-2-cinnamyl-1-(cyclopropane) carbonylpiperidine (formula II; Ar=$C_6H_5$, m=1, n=2, R=cyclopropyl) Yield: 100% $[\alpha]_D=+6.30$ (c=4.5, methylene chloride)

TLC: Rf=0.60–0.75 (95:5 v/v methylene chloride/acetone)

Stage b) (−)-(E)-2-cinnamyl-1-(cyclopropylmethyl) piperidine Yield: 94% $[\alpha]_D=-28.5°$ (c=1, methylene chloride)

TLC: Rf=0.45–0.65 (95:5 v/v methylene chloride/10% ammoniacal MeOH)

NMR: Same as for the racemic compound (Ex. 2A.1).

Hydrochloride: mp=151–152° C. (ethyl ether/isopropanol).

Analysis ($C_{18}H_{26}ClN$): % C, H, Cl, N in agreement.

IR: Same as for the racemic compound (Ex. 2A.1).

Example 2A.4: (E)-2-cinnamyl-1-cyclobutylmethylpiperidine (formula I; Ar=$C_6H_5$, m=1, n=2, R=cyclobutyl)

Stage a) The method is the same as that of Example 1.1, Stage a), the initial reactants being (E)-2-(cinnamyl) piperidine and cyclobutanecarboxylic acid chloride, which furnish (E)-2-cinnamyl-1-(cyclobutanecarbonyl)piperidine (formula II; Ar=$C_6H_5$, m=1, n=2, R=cyclobutyl). Yield: 99%.

TLC: Rf=0.40–0.55 (95:5 v/v methylene chloride/acetone)

Stage b) The intermediate from the preceding stage is reduced under the conditions described in Example 1.1, Stage b) to furnish (E)-2-cinnamyl-1-(cyclobutanecarbonyl)piperidine. Yield: 86%.

TLC: Rf=0.65–0.90 (95:5 v/v methylene chloride/10% ammoniacal MeOH)

NMR: 1.0–2.60 (m, 18H); 2.70–2.80 (m, 2H); 6.10–6.20 (m, 1H); 6.40 (d, 1H); 7.10–7.40 (m, 5H).

Hydrochloride: mp=163° C. (ethyl acetate).

Analysis ($C_{19}H_{28}ClN$): % C, H, Cl, N in agreement;

IR (KBr): 2900, 2500, 1440, 1210, 1080, 980, 860, 700 cm$^{-1}$.

Example 2A. 5: (E) -2-cinnamyl-1- (phenethyl) piperidine (formula I; Ar=$C_6H_5$, m=2, n=2, R= $C_6H_5$)

The compound is prepared as described in Example 1.6 above from (E)-2-(cinnamyl)piperidine and phenylacetic acid chloride.

Stage a) (E) -2-cinnamyl-1-(phenylacetyl)piperidine (formula II; Ar=$C_6H_5$, m=2, n=2, R=$C_6H_5$) Yield: 99%

TLC: Rf=0.50–0.60 (95:5 v/v methylene chloride/acetone)

Stage b) (E)-2-cinnamyl-1-(phenethyl)piperidine Yield: 73%

TLC: Rf=0.60–0.80 (98:2 v/v methylene chloride/10% ammoniacal MeOH)

NMR: 1.30–1.80 (m, 6H); 2.30–2.60 (m, 4H); 2.80–3.00 (m, 5H); 6.10–6.20 (m, 1H); 6.40 (d, 1H); 7.10–7.40 (m, 10H)

Hydrochloride: Hygroscopic compound, m.p.=95–100° C. (ethyl ether/isopropanol)

Analysis ($C_{22}H_{28}ClN$): % C, H, Cl, N in agreement;

IR (KBr): 3400, 2900, 2500, 1600, 1430, 1260, 1080, 740, 690 cm$^{-1}$.

Example 2A.6: (Z)-2-cinnamyl-1-cyclopropylmethylpiperidine (formula I; Ar=$C_6H_5$, m=1, n=2, R=cyclopropyl)

The compound is prepared as described in Example 2A.1 above from (Z)-2-(cinnamyl)piperidine (Preparation 2A, Stage b).

Stage a) (Z)-2-cinnamyl-1-(cyclopropane) carbonylpiperidine (formula II; Ar=$C_6H_5$, m=1, n=2, R=cyclopropyl) Yield: 96%

TLC: Rf=0.75–0.80 (ethyl acetate)

NMR: 0.60–0.85 (m, 2H); 0.85–1.10 (m, 2H); 1.10–1.90 (m, 9H); 2.40–3.00 (m, 2H); 3.80–5.00 (m, 1H); 5.45–5.85 (m, 1H); 6.40–6.70 (m, 1H); 7.10–7.50 (m, 5H).

Stage b) (Z)-2-cinnamyl-1-cyclopropylmethylpiperidine. Yield: 91.2%

TLC: Rf=0.50–0.70 (95:5 v/v methylene chloride/10% ammoniacal MeOH)

NMR: 0.00–0.10 (m, 2H); 0.30–0.60 (m, 2H); 0.60–1.00 (m, 1H); 1.10–1.80 (m, 6H); 2.00–2.65 (m, 6H); 2.90–3.20 (m, 1H); 5.45–5.90 (m, 1H); 6.35–6.60 (m, 1H); 7.10–7.50 (m, 5H).

Hydrochloride: mp=112° C. (ethyl ether).

Analysis ($C_{18}H_{26}ClN$): % C, H, Cl, N in agreement;

IR (KBr): 3400, 2800, 2600, 2500, 1440, 1200, 1020, 1000, 960, 800, 770, 680 cm$^{-1}$.

Example 2B.1: (E)-2-(p-fluorocinnamyl)-1-cyclopropylmethyl-pyrrolidine (formula I-E; Ar=p-fluorophenyl, m=1, n=2, R=cyclopropyl)

In a reactor protected from moisture, there are introduced 2.3 g (0.010 mol) of (E)-2-(p-fluorocinnamyl)piperidine (Preparation 2B) dissolved in 25.2 ml acetonitrile, followed, during 2 min, by 1.56 g (1.1–0.012 mol) bromomethylcyclopropane. The medium is kept stirring at ambient temperature for 1 h 30 min, is raised to 60° C. for 4 h, and is then lowered to 20± 3° C. for 16 h. The solvent is evaporated under vacuum and on a water bath. The oily residue is dissolved in water, acidified and extracted with ether. After decanting, the cooled aqueous phase is alkalinized with soda, extracted with ether and washed with saturated NaCl solution. The organic phase is dehydrated over $Na_2SO_4$ and the solvent is then removed by distillation. The residue is purified by the Chromatoflash technique, elution being carried out with a 90:10 v/v mixture of methylene chloride and 10% ammoniacal MeOH, and is then subjected to a second acid-alkali treatment. (E)-2-(p-fluorocinnamyl)-1-(cyclopropylmethyl)pyrrolidine is obtained in the form of a yellow oil.

Weight: 0.9 g Yield: 31%

TLC: Rf=0.35–0.60 (90:10 v/v methylene chloride/10% ammoniacal MeOH)

NMR: 0.00–0.20 (m, 2H); 0.40–0.60 (m, 2H); 0.70–1.00 (m, 1H); 1.10–1.90 (m, 6H); −2.00–2.70 [sic] (m, 6H); 2.8[sic]–3.20 (m, 1H); 5.90–6.50 (m, 2H) 6.80–7.40 (m, 4H).

Hydrochloride: mp=135° C. (ethyl acetate)
Analysis ($C_{18}H_{25}ClFN$): % C, H, Cl, F, N in agreement;
IR (KBr): 3500, 2850, 2450, 1590, 1500, 1450, 1220, 1000, 860, 520 cm$^{-1}$.

Example 2B.2: (Z)-2-(p-fluorocinnamyl)-1-cyclopropylmethylpiperidine (formula I-Z; Ar=p-fluorophenyl, m=1, n=2, R=cyclopropyl)

The compound is prepared as described in Example 2B.1 above from (Z)-2-(p-fluorocinnamyl)piperidine (Preparation 2B), with a yield of 43%.
TLC: Rf=0.35–0.60 (90:10 v/v methylene chloride/10% ammoniacal MeOH)
NMR: 0.00–0.10 (m, 2H); 0.20–0.60 (m, 2H); 0.60–1.00 (m, 1H); 1.10–1.80 (m, 6H); 2.00–2.60 (m, 6H); 2.80–3.20 (m, 1H); 5.50–5.90 (m, 1H); 6.30–6.60 (m, 1H); 6.90–7.30 (m, 4H).
Hydrochloride: mp=102° C. (ethyl acetate)
Analysis ($C_{18}H_{25}ClFN$): % C, H, Cl, F, N in agreement;
IR (KBr): 3400, 2900, 2400, 1600, 1500, 1440, 1220, 1160, 1000, 1090, 1030, 860, 840, 750, 620, 520 cm$^{-1}$.

Example 2C: (E)-2-(p-chlorocinnamyl)-1-(cyclopropylmethyl)piperidine (formula I; Ar=p-chlorophenyl, m=1, n=2, R=cyclopropyl)

The compound is prepared as described in Example 2B.1 above, from (E)-2-(p-chlorocinnamyl)piperidine (Preparation 2C[)] with a yield of 44%.
NMR: 0.00–0.20 (m, 2H); 0.40–0.60 (m, 2H); 0.60–1.00 (m, 1H); 1.10–1.80 (m, 6H); 2.10–2.80 (m, 6H); 2.90–3.20 (m, 1H); 5.90–6.70 (m, 2H); 7.30 (m, 4H).
Hydrochloride. mp=173° C. (ethyl acetate)
Analysis ($C_{18}H_{25}Cl_2N$): % C, H, Cl, N in agreement;
IR (KBr): 3500, 2900, 2500, 1440, 1080, 970, 950, 850 cm$^{-1}$.

Example 2D: (E)-2-(m-chlorocinnamyl)-1-(cyclopropylmethyl)piperidine (formula I; Ar=m-chlorophenyl, m=1, n=2, R=cyclopropyl)

The compound is prepared as described in Example 1.1 from (E)-2-(m-chlorocinnamyl) piperidine (Preparation 2D).
Stage a) (E)-2-(m-chlorocinnamyl)-1-(cyclopropanecarbonyl)piperidine (formula II; Ar=m-chlorophenyl, m=1, n=2, R=cyclopropyl). Yield: 91%.
Stage b) (E)-2(m-chlorocinnamyl)-1-(cyclopropylmethyl) piperidine. Yield: 95%.
TLC: Rf=0.7 (90:10 v/v methylene chloride/10% ammoniacal MeOH)
NMR: 0.00–0.30 (m, 2H); 0.60–0.70 (m, 2H); 0.90–1.10 (m, 1H); 1.30–1.90 (m, 6H); 2.30–2.80 (m, 6H); 3.10–3.20 (m, 1H); 6.30–6.50 (m, 2H); 7.20–7.50 (m, 4H).
Hydrochloride: mp=129° C. (ethyl acetate).
Analysis ($C_{18}H_{25}Cl_2N$): % C, H, Cl, N in agreement;
IR (KBr): 3400, 2950, 2500, 1590, 1560, 1440, 1210, 970, 780, 680, 560 cm$^{-1}$.

Example 2E: (E)-2-(3,4-dichlorocinnamyl)-1-(cyclopropylmethyl)piperidine (formula I; Ar=3,4-dichlorophenyl, m=1, n=2, R cyclopropyl)

The compound is prepared as described in Example 1.1, from (E)-2-(3,4-dichlorocinnamyl) piperidine (Preparation 2E).
Stage a) (E)-2-(3,4-dichlorocinnamyl)-1-(cyclopropanecarbonyl)piperidine (formula II; Ar=3,4-dichlorophenyl, m=1, n=2, R=cyclopropyl). Yield: 91%.
TLC: Rf=0.90–1.00 (90:10 v/v methylene chloride/10% ammoniacal MeOH).

Stage b) (E)-2-(3,4-dichlorocinnamyl)-1-(cyclopropylmethyl)piperidine. Yield: 79%.
TLC: Rf=0.65–0.80 (90:10 v/v methylene chloride/10% ammoniacal MeOH).
NMR: 0.00–0.20 (m, 2H); 0.40–0.70 (m, 2H); 0.70–1.10 (m, 1H); 1.10–1.80 (m, 6H); 2.10–2.80 (m, 6H); 2.90–3.20 (m, 1H); 6.20–6.40 (m, 2H); 7.10–7.50 (m, 3H).
Hydrochloride: mp=153° C. (ethyl acetate)
Analysis ($C_{18}H_{24}Cl_3N$): % C, H, Cl, N in agreement;
IR (KBr): 3400, 2900, 2500, 1450, 1130, 1020, 990, 820, 800 cm$^{-1}$.

Example 2F: (E)-2 -(p-methylcinnamyl)-1-(cyclopropylmethyl)piperidine (formula I; Ar=p-toluyl, m=1, n=2, R=cyclopropyl)

The compound is prepared as described in Example 1.1, from (E)-2-(p-methylcinnamyl)piperidine (Preparation 2F).
Stage a) (E)-2-(p-methylcinnamyl)-1-(cyclopropane) carbonylpiperidine (formula II; Ar=p-toluyl, m=1, n=2, R=cyclopropyl). Yield: 100%.
Stage b) (E)-2-(p-methylcinnamyl)-1-(cyclopropylmethyl) piperidine. Yield: 98%.
NMR: 0.00–0.20 (m, 2H); 0.40–0.60 (m, 2H); 0.70–1.10 (m, 1H); 1.10–1.90 (m, 6H); 2.35 (s, 3H); 2.10–2.80 (m, 6H); 2.80–3.20 (m, 1H); 5.90–6.50 (m, 2H); 6.90–7.30 (m, 4H).
Hydrochloride: mp=152° C. (ethyl acetate).
Analysis ($C_{19}H_{28}ClN$): % C, H, Cl, N in agreement;
IR (KBr): 3300, 2900, 2500, 1500, 1450, 1420, 1250, 1020, 960, 800, 490 cm$^{-1}$.

Example 2G: (E) -2-p-trifluoromethylcinnamyl)-1-cyclopropylmethylpiperidine (formula I; Ar=p-trifluoromethylphenyl, m=1, n=2, R=cyclopropyl)

The compound is prepared as described in Example 1.1, from (E) -2- (p-trifluoromethylcinnamyl)piperidine (Preparation 2G).
Stage a) (E)-2-(p-trifluoromethylcinnamyl)-1-cyclopropanecarbonylpiperidine (formula II; Ar=p-trifluoromethylphenyl, m=1, n=2, R=cyclopropyl). Yield: 98%.
Stage b) (E)-2-(p-trifluoromethylcinnamyl)-1-cyclopropylmethylpiperidine. Yield; 92%.
TLC: Rf=0.6 (90:10 v/v methylene chloride/10% ammoniacal MeOH)
NMR: 0.00–0.20 (m, 2H); 0.40–0.60 (m, 2H); 0.80–1.00 (m, 1H); 1.20–1.80 (m, 6H); 2.30–2.70 (m, 6H); 3.00–3.10 (m, 1H); 6.20–6.40 (m, 1H) 6.45 (d, 1H); 7.30–7.70 (m, 4H).
Hydrochloride: mp=125° C. (ethyl acetate).
Analysis ($C_{19}H_{25}F_3ClN$): % C, H, F, Cl, N in agreement;
IR (KBr): 2950, 2450, 1430, 1320, 1160, 1120, 1070, 960, 790, 690 cm$^{-1}$.

Example 2H: (E)-2-(p-methoxycinnamyl)-1-cyclopropylmethylpiperidine (formula I; Ar=p-methoxyphenyl, m=1, n=2, R=cyclopropyl)

The compound is prepared as described in Example 1.1, from (E)-2-(p-methoxycinnamyl)piperidine (Preparation 2H).
Stage a) (E)-2-(p-methoxycinnamyl)-1-cyclopropanecarbonylpiperidine (formula II; Ar=p-methoxyphenyl, m=1, n=2, R=cyclopropyl). Yield: 90%.
TLC: Rf=0.90–1.00 (90:10 v/v methylene chloride/10% ammoniacal MeOH)

Stage b) (E)-2-(p-methoxycinnamyl)-1-cyclopropylmethylpiperidine. Yield: 72%.

TLC: Rf=0.80–1.00 (90:10 v/v methylene chloride/10% ammoniacal MeOH)

A final purification step is added, by the Chromatoflash technique on a silica column, with elution by means of a 95:5 v/v mixture of methylene chloride and 10% ammoniacal methanol.

NMR: 0.10–0.30 (m, 2H); 0.40–0.70 (m, 2H); 0.70–1.10 (m, 1H); 1.20–2.00 (m, 6H); 2.00–2.80 (m, 6H); 2.80–3.20 (m, 1H); 3.75 (s, 3H); 5.90–6.50 (m, 2H); 6.70–7.00 (m, 2H); 7.20–7.40 (m, 2H). Analysis ($C_{19}H_{27}NO$): % C, H, N, O in agreement;

IR (NaCl): 2800, 1600, 1500, 1450, 1260, 1170, 1050, 980, 820 $cm^{-1}$.

Example 2I: (E)-2-(1-naphth-1-yl-Propen-3-yl)-1-cyclopropylmethylpiperidine (formula I; Ar=naphth-1-yl, m=1, n=2, R=cyclopropyl)

The compound is prepared as described in Example 1.1 from (E)-2-(1-naphth-1-yl-propen-3-yl)piperidine (Preparation 2I).

Stage a) (E)-2-(1-naphth-1-yl-propen-3-yl)-1-cyclopropanecarbonylpiperidine (formula II; Ar=naphth-1-yl, m=1, n=2, R=cyclopropyl). Yield: 99%.

Stage b) (E)-2-(1-naphth-1-yl-propen-3-yl)-1-cyclopropylmethylpiperidine. Yield: 92%.

TLC: Rf=0.75 (90:10 v/v methylene chloride/10% ammoniacal MeOH)

NMR: 0.00–0.20 (m, 2H); 0.40–0.60 (m, 2H); 0.80–1.00 (m, 1H); 1.10–1.40 (m, 1H); 1.40–1.90 (m, 5H); 2.30–2.80 (m, 6H); 3.00–3.20 (m, 1H); 6.10–6.30 (m, 1H); 7.10 (d, 1H); 7.30–7.60 (m, 4H); 7.70–7.90 (m, 2H); 8.10 (d, 1H).

Hydrochloride: mp=118° C. (ethyl acetate).

Analysis ($C_{22}H_{28}ClN$): % C, H, Cl, N in agreement;

IR (KBr): 3400, 2950, 2450, 1450, 1430, 1210, 1020, 980, 880, 500 $cm^{-1}$.

Example 2J: (E)-2-(1-thien-2-yl-proven-3-yl)-1-cyclopropylmethylpiperidine (formula I; Ar=thien-2-yl, m=1, n=2, R=cyclopropyl)

The compound is prepared as described in Example 1.1 from (E)-2-(1-thien-2-yl-propen-3-yl)piperidine (Preparation 2J)

Stage a) (E)-2-(1-thien-2-yl-propen-3-yl)-1-cyclopropanecarbonylpiperidine (formula II; Ar=thien-2-yl, m=1, n=2, R=cyclopropyl). Yield: 96%.

Stage b) (E)-2-(1-thien-2-yl-propen-3-yl)-1-cyclopropylmethylpiperidine. Yield: 76%.

TLC: Rf=0.8 (90:10 v/v methylene chloride/10% ammoniacal MeOH)

A purification step is added, by the Chromatoflash technique on a silica column, with elution by means of a 95:5 v/v mixture of methylene chloride and 10% ammoniacal methanol.

NMR: 0.00–0.20 (m, 2H); 0.50–0.60 (m, 2H); 0.80–0.90 (m, 1H); 1.20–1.80 (m, 6H); 2.20–2.60 (m, 6H); 3.00–3.10 (m, 1H); 6.00–6.10 (m, 1H); 6.50 (d, 1H); 6.80–7.00 (m, 2H); 7.10 (d, 1H).

Hydrochloride: mp=175–177° C. (ethyl acetate).

Analysis ($C_{16}H_{24}ClNS$): % C, H, Cl, N, S in agreement;

IR: 2980, 2500, 1470, 1210, 980, 830, 740, 560 $cm^{-1}$.

Example 2K: (z)-2-cinnamyl-1-cyclopropylmethylpyrrolidine (formula I-Z; Ar=phenyl, m=1, n=1, R=cyclopropyl)

The compound is prepared as described in Example 1.1 from (Z)-2-(cinnamyl)pyrrolidine (Preparation 2K).

Stage a) (Z)-2-cinnamyl-1-(cyclopropanecarbonyl)pyrrolidine (formula II; Ar=phenyl, m=1, n=1, R=cyclopropyl). Yield: 87%.

TLC: Rf=0.35–0.55 (95:5 v/v methylene chloride/acetone)

Stage b) (Z)-2cinnamyl-1(cyclopropymethyl)pyrrolidine. Yield: 97%.

A purification step is added, by the Chromatoflash technique on a silica column, with elution by means of a 96:4 v/v mixture of methylene chloride and ammoniacal methanol.

TLC: Rf=0.50–0.80 (98:2 v/v methylene chloride/10% ammoniacal MeOH)

NMR: 0.00–0.20 (m, 2H); 0.40–0.60 (m, 2H); 0.80–0.90 (m, 1H); 1.50–2.00 (m, 5H); 2.10–2.20 (m, 1H); 2.30–2.40 (m, 2H); 2.60–2.80 (m, 2H); 3.80–3.90 (m, 1H); 5.60–5.70 (m, 1H); 6.50 (s,1H); 7.10–7.30 (m, 5H).

Hydrochloride: mp=129° C. (ethyl ether/isopropanol).

Analysis ($C_{17}H_{24}ClN$): % C, H, Cl, N in agreement;

IR (KBr): 2900, 2480, 1440, 1180, 1060, 940, 800, 700, 500 $cm^{-1}$.

Example 2L: (E)-2-(p-fluorocinnamyl) -1-cyclopropylmethylpyrrolidine (formula I; Ar=p-fluorophenyl, m=1, n=1, R=cyclopropyl)

The compound is prepared as described in Example 1.1, from (E)-2-(p-fluorocinnamyl)pyrrolidine (Preparation 2L).

Stage a) (E)-2-(p-fluorocinnamyl)-1-cyclopropanecarbonylpyrrolidine. (formula II; Ar=p-fluorophenyl, m=1, n=2, R=cyclopropyl). Yield: 100%.

TLC: Rf=0.400–0.55 (95:5 v/v methylene chloride/acetone)

Stage b) (E)-2-(p-fluorocinnamyl)-1-cyclopropylmethylpyrrolidine. Yield: 84%.

TLC: Rf=0.75–0.95 (90:10 v/v methylene chloride/10% ammoniacal MeOH)

NMR: 0.10–0.20 (m, 2H); 0.40–0.60 (m, 2H); 0.90–1.00 (m, 1H); 1.50–2.10 (m, 5H); 2.10–2.30 (m, 2H); 2.30–2.40 (m, 1H); 2.50–2.60 (m, 1H); 2.70–2.80 (m, 1H); 3.30–3.40 (m, 1H): 6.00–6.20 (m, 1H): 6.40 (d, 1H); 6.90–7.00 (m, 2H); 7.20–7.30 (m, 2H).

IR (NaCl): 2950, 2850, 1600, 1500, 1220, 1160, 980, 840 $cm^{-1}$.

Hydrochloride: The hydrochloride is very hygroscopic.

Analysis ($C_{17}H_{23}ClFN$): % C, H, F, N in agreement.

Pharmacological Studies

The compounds of the invention (I) and their salts show their capacity for interaction with sigma receptors in binding tests carried out in vitro in the presence of a labeled ligand specific for sigma receptors, $(+)[^3H]SKF10.047$. The test of binding to phenylcyclidine receptors (PCP receptors), performed in the presence of a ligand specific for PCP receptors, $[^3H]TCP$, was used to investigate any undesirable interaction of the compounds of the invention with these receptors.

In vivo, the ability of the compounds of the invention (I) to inhibit gastroduodenal ulcers induced by the administration of cysteamine was demonstrated, and in a very favorable manner, by comparison with Igmésine hydrochloride (proposed INN), or (+)-N-(cyclopropylmethyl)-1-ethyl-N-methyl-1,4-diphenyl-3-butene-1-ylamine hydrochloride, a preferred compound of Patent EP 362,001.

In addition, the protection afforded by the compounds of the invention against diarrhea induced experimentally by a bacterial endotoxin, Salmonella lipopolysaccharide, was demonstrated in the mouse.

In Vitro Study

Experiments on binding to sigma and PCP receptors are performed with the ligands $(+)[^3H]SKF10.047$ and $[^3H]$ TCP, respectively, by the technique described by Largent, B. L., et al. in *J. Pharmacol. Exp. Ther.*, 1986, Vol. 238, pp. 739–748. The principle of this technique is to place in competition the affinity of the test substance and that of a radioactive ligand specific for the receptor being studied.

The technique consists in incubating a preparation of rat brain membrane loaded with the labeled ligand specific for the receptor under study in solutions of varying concentration of the test substance. After filtration, one measures the radioactivity of the solution, which represents the displacement of this labeled ligand by the test substance.

The results are expressed as the $IC_{50}$ of the test substance, which is the concentration at which the tritiated ligand is displaced from 50% of its binding sites in the membrane preparation used. Thus, the lower the $IC_{50}$, the greater the affinity of the compound for the receptor. The values obtained are presented in Table 1 below. Haloperidol (INN), which is known, among other properties, for its affinity for σ receptors, is shown by way of reference.

TABLE 1

IN VITRO BINDING TESTS: $IC_{50}$ (nM)

| Receptors Test substances | Sigma | PCP |
|---|---|---|
| Example 1.1 | 34.25 | >10,000 |
| Example 1.4 | 4.52 | >10,000 |
| Example 2A.6 | 34.3 | >10,000 |
| Haloperidol | 8.95 | 1.268 |

These results show that the compounds (I) of the invention have a strong affinity for sigma receptors, especially in the case of the compound of Example 1.4. In addition, in comparison to haloperidol, the compounds (I) of the invention show an affinity for PCP receptors that may be regarded as zero.

In a second series of experiments, the $IC_{50}$ of other compounds of the invention was determined with regard to [$^3$H]SKF10.047 in rat brain membranes and this value was compared with the $IC_{50}$ of haloperidol, based on the ratio of the $IC_{50}$ of haloperidol to the $IC_{50}$ of the compound under test. The results are given in Table 2.

TABLE 2

IN VITRO SIGMA BINDING TESTS IN COMPARISON TO HALOPERIDOL

| Compounds tested | $IC_{50}$, haloperidol $IC_{50}$, example |
|---|---|
| Ex. 1.3 | 1.6 |
| Ex. 1.5 | 0.8 |
| Ex. 1.6 | 1.3 |
| Ex. 2A.3 | 1.4 |
| Ex. 2A.4 | 2.3 |
| Ex. 2A.5 | 1.0 |
| Ex. 2B.2 | 1.6 |
| Ex. 2G | 0.8 |
| Ex. 2K | 4.3 |
| Ex. 2L | 1.1 |

These results confirm that the compounds (I) of the invention have a strong affinity for sigma receptors characterized by [$^3$H]SKF10.047, equal to or greater than that of haloperidol and in some cases approximately 2 to 4 times greater.

In conclusion, these results provide convincing evidence of the high affinity of the compounds of the invention for sigma receptors. This affinity is, moreover, accompanied by a remarkable specificity, since these compounds, unlike haloperidol, do not interfere with PCP receptors.

In vivo Study: Cysteamine-induced Gastroduodenal Ulcer

The activity of the compounds of the invention with respect to the gastrointestinal tract was shown in the rat by their ability to inhibit gastroduodenal ulcers induced by the administration of cysteamine. In terms of practical methodology, the study is performed according to the method described by Robert, A., et al., in *Digestion*, 1974, Vol. 11, pp. 199–214, in groups of male Sprague-Dawley rats with an average weight of 200 g, to which a cysteamine hydrochloride solution is administered by subcutaneous injection in a dose of 400 mg/kg. The test compounds are administered to the animals 1 h or 30 min, respectively, before the ulcerogenic agent, depending on whether the oral or intraperitoneal route is used. Eighteen hours later, the rats are sacrificed by elongation; the stomach and duodenum are removed, rinsed with physiological salt solution, and pinned to a card. The antropyloroduodenal region is examined for ulcers, and the area of the ulcers, expressed in $mm^2$, is determined by multiplying the two main perpendicular axes of the lesion. Statistical analysis of the results is performed by means of Student's t-test for the ulcerated areas in comparison with a control group. The results obtained after intraperitoneal administration are presented in Table 3 and are expressed as the $ED_{50}$, which is the effective dose (mg/kg) of compound inhibiting 50% of the cysteamine-induced ulcers. Igmésine is presented by way of comparison.

TABLE 3

CYSTEAMINE-INDUCED ULCER: $ED_{50}$ BY THE I. P. ROUTE

| Compounds tested (mg/kg) | $ED_{50}$ |
|---|---|
| Example 1.1 | 0.185 |
| Example 1.2 | <0.100 |
| Example 1.3 | <0.100 |
| Example 1.4 | 0.137 |
| Example 2A.1 | 0.100 |
| Example 2A.2 | <0.100 |
| Example 2A.6 | <0.100 |
| Igmesine | 5.950 |

The compounds of the invention are conclusively demonstrated to be 30 to 60 times more active than this compound of prior art to which they are compared.

Diarrhea Induced by Salmonella Lipopolysaccharide.

The activity of the compounds of the invention in a model of secretory diarrhea induced by *Salmonella enteritidis* lipopolysaccharide (LPS) was studied according to a protocol inspired by Ciancio, M. J., et al., *Gastroenterology*, 1992, Vol. 103, pp. 1437–1443. Male $dBA_2$ mice ranging in weight from 20 to 25 g, placed in individual grid-bottomed cages, were administered the test compound orally 1 h with the injection of *S. enteridis* LPS (Ref. L6761 Sigma) in a dose of 15 mg/kg i.v. A preweighed filter paper was placed under each cage in order to weigh the feces eliminated over a period of 2 h. The $ED_{50}$ was calculated, this being the dose that reduced the increase in feces caused by the LPS by 50% in comparison with a control group given the endotoxin alone.

The tested compounds (I) of the invention showed especially advantageous activity in this model, with $ED_{50}$s that were generally below 100 µg/kg.

These results point to the potential use of the compounds of the invention for the symptomatic treatment of diarrheas with a secretory component and of diverse etiologies: toxic, infectious including viral, inflammatory, and post-antibiotic, as well as diarrheas following organic disease of the mucosa.

The acute toxicity of the compounds of the invention was determined after oral administration in the rat. On this basis it was possible to determine their approximate $LD_{50}$, which is the lethal dose for 50% of the animals under the conditions of the experiment. This toxicity was considered to be negligible at doses more than one hundred times the physiologically active dose of these compounds.

Formulations

As described, these pharmacological properties combined with the low toxicity of the compounds of the invention make it possible to envision their usefulness as medicinal drugs for the prevention or treatment of i) neurological disorders, especially psychotic states, depressive states, memory and behavioral disturbances, stress and anxiety, as well as ii) disorders of the gastrointestinal tract, such as, for example, certain forms of gastroduodenal ulcer, or diarrhea, especially with a secretory component.

The dosages normally range from 0.1 to 1000 mg, and more especially 1 to 500 mg, of compound, depending on the nature and severity of the complaint to be treated. These daily therapeutic doses may be divided into several portions. Generally speaking, a daily dosage of 5 mg to 250 mg of compound, divided into two to four portions, yields a satisfactory therapeutic result.

The compounds of the invention are administered to the patients to be treated in the form of medications whose nature is suited to the complaint to be treated.

The medicinal preparations will be, as non-restrictive examples, tablets, dragées, capsules, powders, solutions, suspensions, gels or suppositories, depending on the case. These various pharmaceutical dosage forms are prepared from the compounds in base form or in the form of their salts and according to methods commonly employed in pharmaceutical practice.

Generally, in medicinal forms of a "solid" nature, the active principle represents from 2 to 50% by weight of the total of the finished dosage form, while the excipients represent from 98 to 50%. For "liquid" dosage forms or those which may be considered liquid, the amount of active principle is between 0.1 and 10% by weight of the finished dosage form, while the excipients may represent 99.9 to 90% by weight of this dosage form.

The formula and the preparation of tablets and of isotonic solution with the compounds of Example 1.4 are described by way of illustration.

Tablets

Formula:

| | |
|---|---|
| Active principle (compound of Example 1.4) | 5.0 to 25.0 mg |
| Polyvinylpyrrolidone | 20.0 mg |
| Carboxymethyl starch | 8.0 mg |
| Magnesium stearate | 2.0 mg |
| Colloidal silica | 0.4 mg |
| Lactose, sufficient quantity for | 200.0 mg |

Preparation

The active principle, in aqueous alcohol solution, is mixed with lactose and then granulated with polyvinylpyrrolidone, also in solution. The particles are dried and sieved through a screen with a mesh opening of 1 mm. The carboxymethyl starch is mixed with the colloidal silica and then added to the granules. This mixture is then mixed intimately with the magnesium stearate and tableted in a dose of 200.0 mg per tablet.

Injectable Isotonic Solution

Formula:

| | |
|---|---|
| Active substance (I), the hydrochloride of Ex. 1.4 | 10.0 mg |
| Sodium chloride | 9.0 mg |
| Distilled water, sufficient quantity for | 1.0 ml |

Preparation

The isotonic solution is distributed in ampuls of suitable volume, which, after sealing, are sterilized by customary thermal means, or alternatively the solution is sterilized by filtration and distributed in ampuls which are then sealed, all of these operations being carried out in a sterile atmosphere.

What is claimed is:

1. The compounds:

(+)-(E)-2-cinnamyl-1-cyclopropylmethylpyrrolidine;

(+)-(E)-2-cinnamyl-1-cyclopropylmethylpyrrolidine;

(−)-(E)-2-cinnamyl-1-cyclopropylmethylpyrrolidine;

(E)-2-cinnamyl-1-cyclobutylmethylpyrrolidine;

(E)-2-cinnamyl-1-cyclopropylethylpyrrolidine; or (E)-2-cinnamyl-1-phenethylpyrrolidine.

2. The compounds:

(E)-2-cinnamyl-1-cyclopropylmethylpiperadine;

(+)-(E)-2-cinnamyl-1-(cyclopropylmethyl)piperadine;

(−)-(E)-2-(cinnamyl)cyclopropylmethylpiperadine;

(E)-2-cinnamyl-1-cyclobutylmethylpiperadine;

(E)-2-cinnamyl-1-(phenethyl)piperadine;

(Z)-2-cinnamyl-cyclopropylmethylpiperadine;

(E)-2-(p-fluorocinnamyl)-1-cyclopropylmethylpyrrolidine;

(Z)-2-(p-fluorocinnamyl)-1-cyclopropylmethylpiperadine;

(E)-2-(p-chlorocinnamyl)-1-(cyclopropylmethyl)piperidine; or (E)-2-(m-chlorocinnamyl)-1-(cyclopropylmethyl)piperidine.

3. The compounds:

(E)-2-(3,4-dichlorocinnamyl)-1-(cyclopropylmethyl)piperidine;

(E)-2-(p-methylcinnamyl)-1-(cyclopropylmethyl)piperidine;

(E)-2-(p-trifluoromethylcinnamyl)-1-cyclopropylmethylpiperidine;

(E)-2-(p-methoxycinnamyl)-1-cyclopropylmethylpiperidine;

(E)-2-(1-naphth-1-yl-propen-3-yl)-1-cyclopropylmethylpiperidine;

(E)-2-(1-thien-2-yl-propen-3-yl)-1-cyclopropylmethylpiperidine;

(Z)-2-cinnamyl-1-cyclopropylmethylpyrrolidine; or (E)-2-(p-fluorocinnamyl)-1-cyclopropylmethylpyrrolidine.

4. A method of treating psychotic states, the method comprising administering to a subject in need of such treatment a therapeutically effective amount of a compound of Formula I

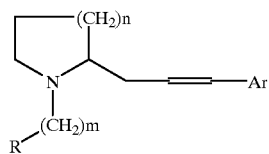

(I)

wherein
- Ar is aryl or heteroaryl, optionally mono-, di-, or tri-substituted with a halogen, nitro, lower alkyl, lower haloalkyl, lower alkoxy or lower haloalkoxy group;
- m has the value of 1 or 2;
- n has the value of 1 to 3;
- R is phenyl, optionally substituted with a halogen, nitro, lower alkyl, lower haloalkyl, lower alkoxy, or lower haloalkoxy group or a cycloalkyl group containing 3 to 7 carbon atoms, an optical or geometric isomer thereof, a derivative in which an atom is replaced by a radioactive isotope, and an addition salt with a pharmaceutically acceptable acid.

5. A method of treating diarrhea, the method comprising administering to a subject in need of such treatment a therapeutically effective amount of a compound of Formula I

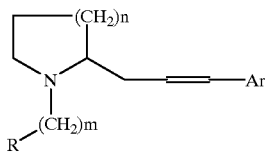

(I)

wherein
- Ar is aryl or heteroaryl, optionally mono-, di-, or tri-substituted with a halogen, nitro, lower alkyl, lower haloalkyl, lower alkoxy or lower haloalkoxy group;
- m has the value of 1 or 2;
- n has the value of 1 to 3;
- R is phenyl, optionally substituted with a halogen, nitro, lower alkyl, lower haloalkyl, lower alkoxy, or lower haloalkoxy group or a cycloalkyl group containing 3 to 7 carbon atoms, an optical or geometric isomer thereof, a derivative in which an atom is replaced by a radioactive isotope, and an addition salt with a pharmaceutically acceptable acid.

* * * * *

UNITED STATES PATENT AND TRADEMARK OFFICE
CERTIFICATE OF CORRECTION

PATENT NO. : 6,013,656
DATED : January 11, 2000
INVENTOR(S) : Calvet et al.

It is certified that error appears in the above-identified patent and that said Letters Patent is hereby corrected as shown below:

Column 3, line 35, after the word "di" insert -- - or --.

Column 4, line 15, after the word "di" insert -- - or --.

Column 5, line 51, "bromine:" should read "bromine.".

Column 9, line 61, "Preparations 2" should read "Preparation 2".

Column 21, line 29, "2C[)]" should read "2C)".

Column 26, line 50, delete "with" and insert -- after --.

Column 26, line 51, "enteridis" should read "enteritidis".

Column 28, line 19, "(+)" should read "(±)".

Signed and Sealed this

Twenty-first Day of November, 2000

Attest:

Q. TODD DICKINSON

Attesting Officer

Director of Patents and Trademarks